United States Patent [19]

Guillaumet et al.

[11] Patent Number: 5,376,661
[45] Date of Patent: Dec. 27, 1994

[54] 3-AMINOCHROMAN SPIRO COMPOUNDS

[75] Inventors: Gérald Guillaumet, Orleans; Tchao Podona, Orleans la Source; Gérard Adam, Le Mesnil le Roi; Béatrice Guardiola, Neuilly sur Seine; Pierre Renard, Versailles, all of France

[73] Assignee: Adir et Compagnie, Courbevoie, France

[21] Appl. No.: 36,329

[22] Filed: Mar. 24, 1993

[30] Foreign Application Priority Data

Apr. 1, 1992 [FR] France .................. 92 03935

[51] Int. Cl.[5] .................. C07D 471/20; A61K 31/44
[52] U.S. Cl. .................. 514/278; 546/16; 546/17
[58] Field of Search .................. 546/16, 17; 514/278

[56] References Cited

PUBLICATIONS

Wade, Organic Chemistry, p. 349 Prentice–Hall publishers (1987).

Martindale, The Extra Pharmacopoeia, *Thirtieth Edition*, p. 628 (1993).

*Primary Examiner*—Alan L. Rotman
*Attorney, Agent, or Firm*—Gordon W. Hueschen

[57] ABSTRACT

The invention relates to a compound selected from those of formula (I):

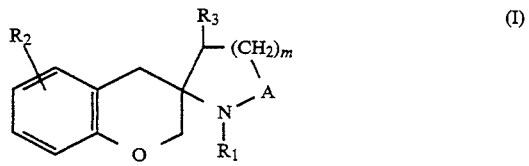

in which $R_1$, $R_2$, $R_3$, A and m are as defined in the description.

Medicinal product which is useful for treating depression and anxiety.

7 Claims, No Drawings

3-AMINOCHROMAN SPIRO COMPOUNDS

The present invention relates to new 3-aminochroman spiro compounds, to processes for their preparation and to pharmaceutical compositions containing them.

3-Aminochroman, 3-aminothiochroman and some of their derivatives are known to be ligands for the receptors of the central nervous system, more particularly of the serotoninergic system, and this makes them usable for the treatment of anxiety, of depression and more particularly of disorders of the central nervous system (European Patents EP 279,150 and EP 222,996). The compounds described in these patents have a certain affinity for the 5-$HT_{1A}$ receptors but also for the D2 receptors, and this results in very low selectivity.

Spiro compounds derived from 2-aminotetralin (a) (J. Med. Chem. (1978) 21 (6) pp 585–7 and J. Pharm. Pharmacol. (1976) 28 suppl. pp 83 P) and from 3-aminoquinoline (b) (Patent FR 2,255,067 and Yakugaku Zasshi (1974) 94 (12) pp 1566–73) are also known in the literature

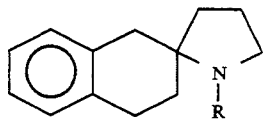

R = H, $CH_3$ (a)

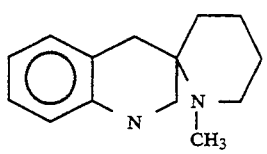

(b)

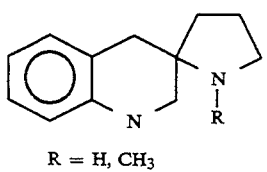

R = H, $CH_3$

These compounds are described above all as antalgic, spasmolytic and antihistaminic agents, with, in the case of the tetralin compounds, also a very slight antidepressant component.

Spiro[pyrrolidine-2,3'-chroman] (c) also described in the literature, without any information other than its structure.

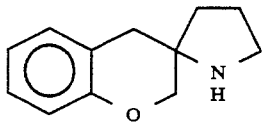

(c)

The compounds of the present invention, which are 3-aminochroman spiro compounds, apart from the fact that their structures are new, have remarkable pharmacological properties.

These are, in fact, powerful ligands for 5-$HT_{1A}$ receptors. This high affinity is all the more interesting since it is backed by a high selectivity in favor of 5-$HT_{1A}$ receptors when compared with dopaminergic and alpha adrenergic receptors and with other serotoninergic receptors (5-HT1B, 5-$HT_{1C}$, 5-$HT_{1D}$, 5-$HT_2$).

These remarkable pharmacological properties render the compounds of the present invention usable in the treatment of disorders of the central nervous system, especially of the serotoninergic system, such as depression, stress, psychosis, anxiety, schizophrenia, as well as of pain, migraines, hypertension and cerebral ischemia. These compounds may also be of interest as modifiers of the alimentary and sexual behavior.

More specifically, the present invention relates to the compounds of general formula (I):

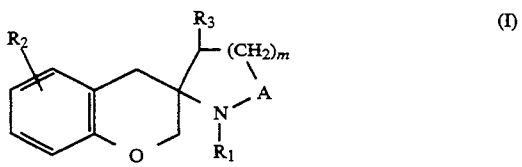

in which:
m, an integer, can assume the values 1 or 2,
A denotes a methylene ($CH_2$) or a carbonyl (CO),
$R_1$ denotes:
a hydrogen,
a group —CO—$R_4$ with $R_4$ denoting a linear or branched alkyl with 1 to 6 carbon atoms, an optionally substituted phenyl or an optionally substituted phenylalkyl whose alkyl chain contains from 1 to 3 carbon atoms,
or a linear or branched alkyl with 1 to 6 carbon atoms, optionally substituted by:
a nitrile,
an optionally substituted phenyl,
a group —$NR_5R_6$ with $R_5$ denoting a hydrogen or a linear or branched alkyl with 1 to 6 carbon atoms and $R_6$ denoting a hydrogen, a linear or branched alkyl with 1 to 6 carbon atoms, optionally substituted by an optionally substituted phenyl, a linear or branched alkylcarbonyl group containing from 2 to 7 carbon atoms, an optionally substituted benzoyl group, an optionally substituted phenylalkylcarbonyl group whose alkyl chain contains from 1 to 3 carbon atoms, a linear or branched alkylsulfonyl group with 1 to 6 carbon atoms, or an optionally substituted phenylsulfonyl group,
any one of the following groups:

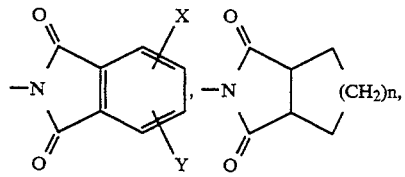

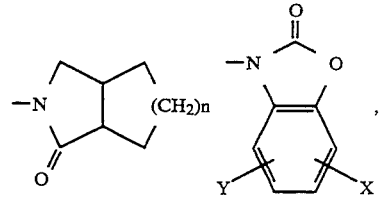

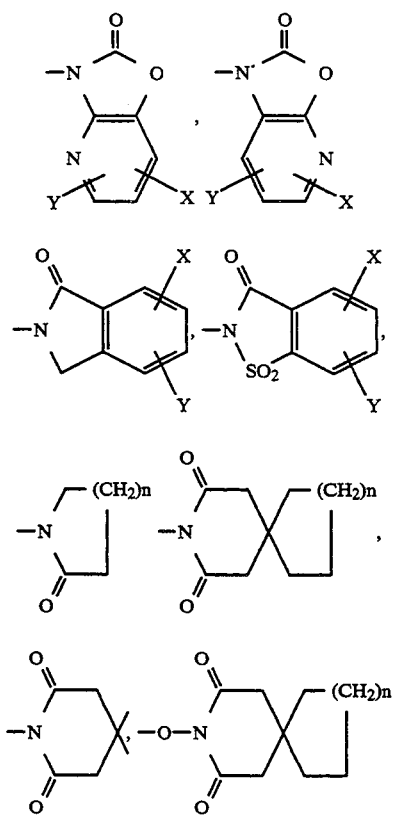

in which:
- X and Y, which are identical or different, denote a hydrogen, a halogen, a hydroxyl, a linear or branched alkyl with 1 to 4 carbon atoms, a linear or branched alkoxy with 1 to 4 carbon atoms,
- n, an integer, can assume the values 1 or 2
- $R_2$ denotes:
  a hydrogen,
  an acetyl group,
  a $CF_3SO_2$—O— group
  or a group —$OR_7$ with $R_7$ having the same definition as $R_1$,
- $R_3$ denotes a hydrogen or a linear or branched alkyl with 1 to 4 carbon atoms, provided that when $R_1=R_2=R_3=H$ then m cannot be equal to 1,
- the expression "optionally substituted" associated with the phenyl, phenylalkyl, phenylsulfonyl, benzoyl or phenylalkylcarbonyl terms means that the aromatic nucleus may be substituted by one or a number of lower alkyls with 1 to 4 carbon atoms, branched or otherwise, nitro, lower alkoxy with 1 to 4 carbon atoms, halogen, trifluoromethyl or hydroxyl,
- their isomers, diastereoisomers and enantiomers, isolated or in mixture form,
- their salts of addition to a pharmaceutically acceptable inorganic or organic acid.

The invention also extends to the process for obtaining the compounds of general formula (Ia):

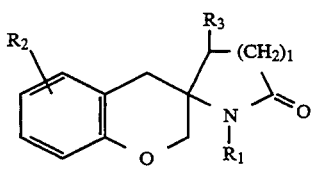

which $R_1$, $R_2$ and $R_3$ are as defined in formula (I), a particular case of the compounds of formula (I) in which compounds m is equal to 1 and A denotes a carbonyl (CO), wherein a substituted benzaldehyde of general formula (II):

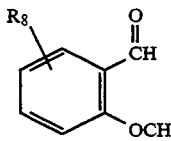

in which $R_8$ denotes a hydrogen or a linear or branched alkoxy with 1 to 6 carbon atoms is reacted at a temperature of between $-5°$ and $0°$ C., with boron tribromide so as to obtain the compound of general formula (III):

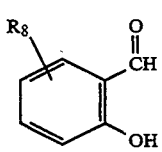

in which $R_8$ has the same meaning as above, which is reacted with heating and in the presence of a substituted ammonium salt with 2-nitroethanol, so as to obtain the compound of general formula (IV):

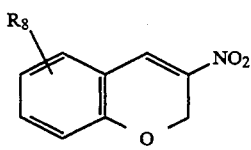

in which $R_8$ has the same meaning as above, which is reduced so as to obtain the compound of general formula (V):

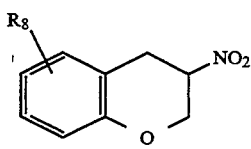

in which $R_8$ has the same meaning as above, which is reacted in the presence of benzyltrimethylammonium methylate in alcoholic medium with an acrylic compound of general formula (VI):

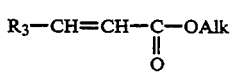

in which $R_3$ has the same meaning as above and Alk denotes an alkyl with 1 to 4 carbon atoms, so as to obtain the compounds of general formula (VIIa):

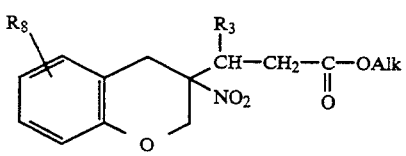
(VIIa)

in which $R_3$, $R_8$ and Alk have the same meaning as above, which is reduced in the presence of Raney nickel and under hydrogen atmosphere so as to obtain, after isolation and optional purification, the spiro compound of general formula (VIIIa):

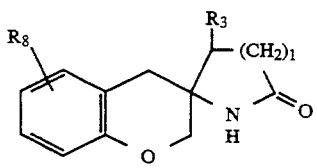
(VIIIa)

in which $R_3$ and $R_8$ have the same meaning as above, which can be reacted in the presence of a strong base with a compound of general formula (IX):

$$Hal'R'_1 \qquad (IX)$$

in which $R'_1$ has the same meaning as $R_1$ in formula (I), provided that $R'_1$ cannot denote a hydrogen, and Hal' denotes a halogen atom, so as to obtain, after isolation and optional purification, the compound of general formula (Xa):

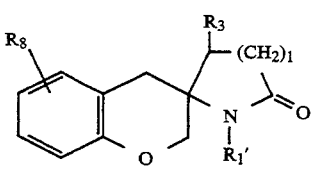
(Xa)

in which $R'_1$, $R_3$ and $R_8$ have the same meaning as above, compounds of formula (VIIIa) and (Xa) which may be treated, in the case where $R_8$ denotes an alkoxy, with an aqueous solution containing hydrobromic acid, to obtain, after isolation and optional purification, the compound of general formula (XIa):

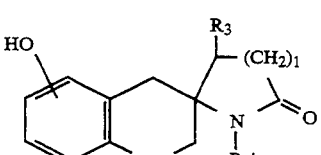
(XIa)

in which $R'_1$ and $R_3$ have the same meaning as above, which can be reacted with a compound of general formula (XII):

$$Hal''—R'_7 \qquad (XII)$$

in which Hal'' denotes a halogen atom and $R'_7$ has the same meaning as $R_7$ in formula (I), provided that $R'_7$ cannot denote a hydrogen, so as to obtain, after isolation and optional purification, the compound of general formula (XIIIa):

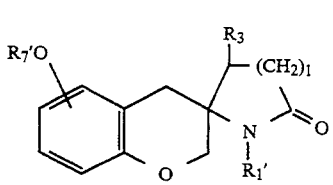
(XIIIa)

in which $R'_1$, $R_3$ and $R'_7$ have the same meaning as above, it being understood that the compounds of general formula VIIIa, Xa, XIa and XIIIa form part of the invention, constitute the compounds of general formula (Ia) such as are defined above, and can, if desired, be purified, separated into their isomers, or, if possible, converted into salts with a pharmaceutically acceptable acid.

The invention also extends to the process for obtaining the compounds of general formula (Ib):

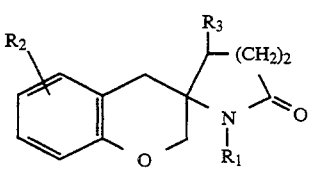
(Ib)

in which $R_1$, $R_2$ and $R_3$ are as defined in formula (I), a particular case of the compounds of formula (I) in which compounds m is equal to 2 and A denotes a carbonyl (CO), wherein a compound of formula (V):

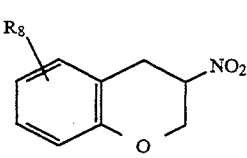
(V)

in which $R_8$ denotes a hydrogen or a linear or branched alkoxy with 1 to 6 carbon atoms is reacted with a halo ester of general formula (X):

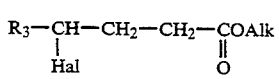
(X)

in which $R_3$ has the same meaning as above, Alk denotes an alkyl with 1 to 4 carbon atoms and Hal denotes a halogen atom, so as to obtain the compounds of general formula (VIIb):

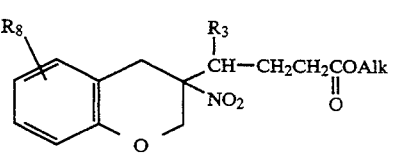
(VIIb)

in which $R_3$, $R_8$ and Alk have the same meaning as above, which are reduced, in the presence of Raney nickel and under hydrogen atmosphere, so as to obtain, after isolation and optional purification, the spiro compound of general formula (VIIIb):

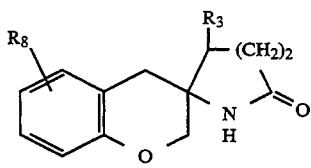

in which $R_3$ and $R_8$ have the same meaning as above, which can be reacted in the presence of a strong base with a compound of general formula (IX): in which $R'_1$ has the same meaning as $R_1$ in formula (I), provided that $R'_1$ cannot denote a hydrogen and Hal' denotes a halogen atom, so as to obtain, after isolation and optional purification, the compound of general formula (Xb):

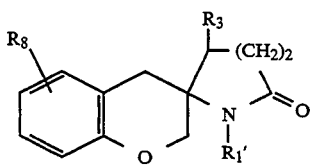

in which $R'_1$, $R_3$ and $R_8$ have the same meaning as above, compounds of formula (VIIIb) and (Xb) which may optionally be treated, in the case where $R_8$ denotes an alkoxy, with an aqueous solution containing hydrobromic acid, to obtain, after isolation and optional purification, the compound of general formula (XIb):

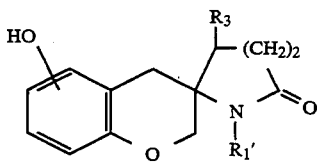

in which $R'_1$ and $R_3$ have the same meaning as above, which can be reacted with a compound of general formula (XII):

 (XII)

in which Hal" denotes a halogen atom and $R'_7$ has the same meaning as $R_7$ in formula (I), provided that $R'_7$ cannot denote a hydrogen, so as to obtain, after isolation and optional purification, the compound of general formula (XIIIb):

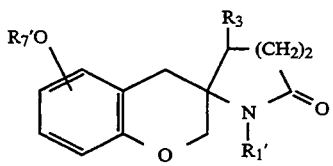

in which $R'_1$, $R_3$ and $R'_7$ have the same meaning as above, it being understood that the compounds of general formula VIIIb, Xb, XIb and XIIIb form part of the invention, form the compounds of general formula (Ib) such as are defined defined above, and can, if desired, be purified, separated into their isomers, or, if possible, converted into salts with a pharmaceutically acceptable acid.

The invention also extends to the process for obtaining the compounds of general formula (Ic):

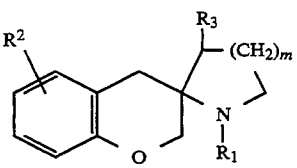

in which $R_1$, $R_2$, $R_3$ and m are as defined in formula (I), a particular case of the compounds of formula (I) in which compounds A denotes a methylene ($CH_2$), wherein a compound of formula (VIII):

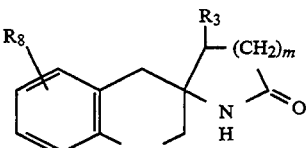

in which $R_3$ and m are as defined above and $R_8$ denotes a hydrogen or a linear or branched alkoxy with 1 to 6 carbon atoms, is reduced in aprotic medium by a reducing agent, so as to obtain, after isolation and optional purification, the compound of general formula (XIV):

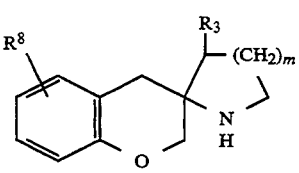

in which $R_3$, $R_8$ and m have the same meaning as above, which can be reacted with a compound of general formula (IX):

 (IX)

in which $R'_1$ has the same meaning as $R_1$ in formula (I), provided that $R'_1$ cannot denote a hydrogen and Hal denotes a halogen atom, so as to obtain, after isolation and optional purification, the compound of general formula (XV):

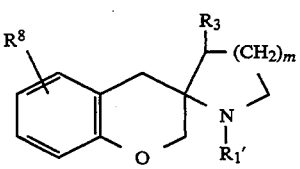

in which $R'_1$, $R_3$, $R_8$ and m have the same meaning as above, compounds of formula (XIV) and (XV) which can be treated, in the case where $R_8$ denotes an alkoxy, with an aqueous solution containing hydrobromic acid, to obtain, after isolation and optional purification, the compound of general formula (XVI):

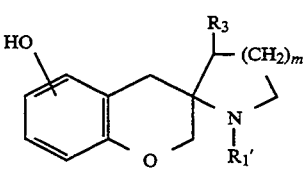

in which R'₁, R₃ and m have the same meaning as above, which can be reacted with a compound of general formula (XII):

Hal''—R'₇ (XII)

in which Hal'' denotes a halogen atom and R'₇ has the same meaning as R₇ in formula (I), provided that R'₇ cannot denote a hydrogen, so as to obtain, after isolation and optional purification, the compound of general formula (XVII):

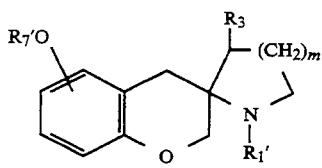

in which R'₁, R₃, R'₇ and m have the same meaning as above, it being understood that the compounds of general formula XIV, XV, XVI and XVII form part of the invention, constitute the compounds of general formula (Ic) and can, if desired, be purified, separated into their isomers or, if possible, converted into salts with a pharmaceutically acceptable acid.

The invention also extends to the process for obtaining the compounds of general formula (Id):

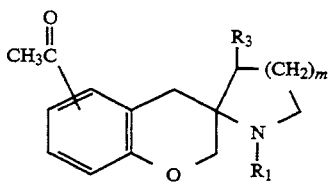

in which R₁, R₃ and m are as defined in formula (I), a particular case of the compounds of formula (I) in which compounds R₂ denotes an acetyl group, wherein a compound of general formula (XVIII):

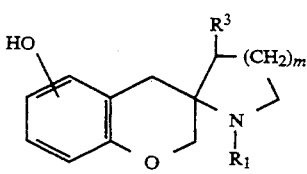

in which R₁, R₂ and m are as defined above, is reacted with trifluoromethanesulfonic anhydride so as to obtain the trifluoromethylsulfonyloxy compound of general formula (XIX):

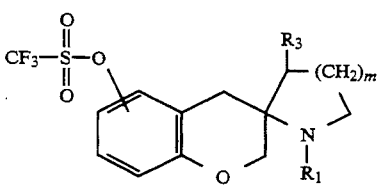

in which R₁, R₃ and m have the same definition as above, which is next treated in aprotic medium with butyl vinyl ether in the presence of triethylamine, of 1,2-bis(diphenylphosphino)ethane and of Pd(OAc)₂ so as to obtain, after isolation and purification, the acetylated compound of general formula (XX):

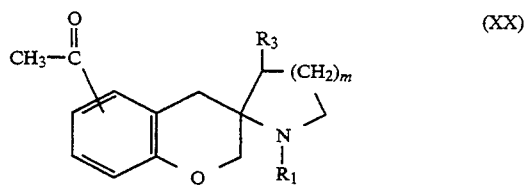

in which R₁, R₃ and m have the same meaning as above, it being understood that the compounds of general formula XIX and XX form part of the invention and can, if desired, be purified, separated into their isomers or, if possible, converted into salts with a pharmaceutically acceptable acid.

The compounds of general formula (I) and their salts of addition to a pharmaceutically acceptable inorganic or organic acid, are powerful ligands for 5-HT$_{1A}$ receptors, with an agonist or antagonist activity in the central nervous system.

This high affinity which is backed by a very high selectivity for these receptors in relation to the D₂, α₂ receptors and to the other serotoninergic receptors renders these compounds of great interest for the treatment of stress, of anxiety, of depression, of psychosis, of schizophrenia, of pain, of cardiovascular disorders, of hypertension, of migraines and of cerebral ischemia.

They can also modify alimentary and sexual behavior.

The compounds of general formula (I) and their salts of addition to a pharmaceutically acceptable inorganic or organic acid, such as, for example, hydrochloric, methanesulfonic, nitric, maleic and similar acids, can be presented in the form of pharmaceutical compositions, using known processes, such as, for example: tablets, gelatin tablets, coated pills, injectable solutions, drinkable solutions or suspensions, emulsions and suppositories.

Besides the inert, nontoxic and pharmaceutically acceptable excipients such as, for example, distilled water, glucose, lactose, starch, talc, vegetable oils, ethylene glycol and the like, these compositions may also contain preserving agents.

The pharmaceutical compositions thus obtained also form part of the invention and, depending on the disorders being treated, the age and the weight of the patient, may contain from 0.1 to 100 mg of active substance in the case of a treatment with 1 to 3 doses per 24 hours.

The following examples illustrate the invention and do not limit it in any way.

PREPARATION 1:
N-(4-BROMOBUT-1-YL)-8-AZASPIRO[4,5]DECANE-7,9-DIONE

Add 7.43 g (53.8 mmol) of potassium carbonate, 4.26 g (19.73 mmol) of 1,4-dibromobutane and a catalytic quantity of potassium iodide to a solution of 3 g (17.94 mmol) of 8-azaspiro[4,5]decane-7,9-dione.

Heat to 60° C. for 6 hours and then cool and remove acetonitrile by evaporation at reduced pressure.

After hydrolysis with 10 cm³ of water, extract the product with methylene chloride and then, after drying and final drying, purify the crude product by chromatography on a silica column (eluent: methylene chloride).

N-(4-Bromobut-1-yl)-8-azaspiro[4,5]decane-7,9-dione is finally obtained in the form of oil in a yield of 69%.

Infrared (film): 1660 and 1720 cm$^{-1}$ v C=O $^1$H NMR 300 MHz (CDCl$_3$) δ: ppm

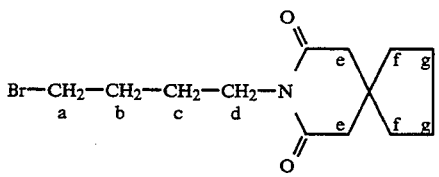

1.45 to 1.52, multiplet, 4H, 2 CH$_2$ 1.45 to 1.52, multiplet, 6H, 3 CH$_2$ 1.79 to 1.90, multiplet, 2H, H$_c$ 2.60, singlet, 4H, H$_e$ 3.42, triplet J=7.1 Hz, 2H, Ha 3.80, triplet J=7.1 Hz, 2H, Hd

PREPARATION 2 and 3

By proceeding in the same way as in the case of preparation 1 but replacing 1,4-dibromobutane with:

1,5-dibromobutane, N-(5-bromopent-1-yl)-8-azaspiro[4,5]decane-7,9-dione is obtained in a yield of 50%.

Infrared (film): 1655 and 1715 cm$^{-1}$ v C=O $^1$H NMR 300 MHz (CDCl$_3$) δ: ppm

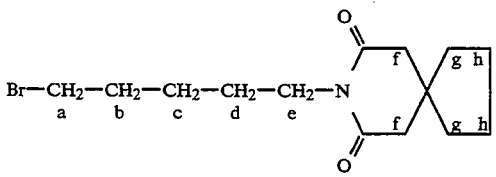

1.35 to 1.73, multiplet, 12H, 6 CH$_2$ 1.81 to 1.90, multiplet, 2H, CH$_2$ 2.57, singlet, 4H, Hf 3.38, triplet J=7.1 Hz, 2H, Ha 3.74, triplet J=7.1 Hz, 2H, He 1,3-dibromopropane, N-(3-bromoprop-1-yl)-8-azaspiro[4,5]decane-7,9-dione is obtained in a yield of 70%.

Infrared (film): 1665 and 1720 cm$^{-1}$ v C=O $^1$H NMR 300 MHz (CDCl$_3$) δ: ppm

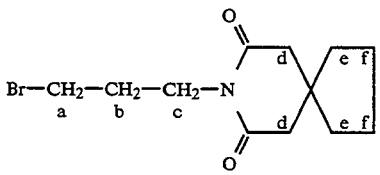

1.45 to 1.56, multiplet, 4H, 2 CH$_2$ 1.66 to 1.75, multiplet, 4H, 2 CH$_2$ 2.06 to 2.19, multiplet, 2H, Hb 2.59, singlet, 4H, Hd 3.36, triplet J=7.1 Hz, 2H, Ha 3.89, triplet J=7.1 Hz, Hc

PREPARATION 4:
N-(2-BROMOETHYL)-8-AZASPIRO[4,5]DECANE-7,9-DIONE

Add 0.65 g (26.9 mmol) of sodium hydride to a solution of 3 g (17.94 mmol) of 8-azaspiro[4,5]decane- 7,9-dione in 30 cm$^3$ of anhydrous N,N-dimethylformamide.

Stir at 60° C. for 1 hour then add 20.21 g (107.6 mmol) of 1,2-dibromoethane and a catalytic quantity of potassium iodide.

Continue heating for one hour after the addition and then, after cooling, remove the solvent at reduced pressure and then, after aqueous hydrolysis, extract the product with methylene chloride and purify the crude product obtained by chromatography on a silica column.

N-(2-Bromoethyl)-8-azaspiro[4,5]decane-7,9-dione is thus obtained in a yield of 63%.

Infrared (film): 1660 and 1715 cm$^{-1}$ v C=O $^1$H NMR 300 MHz (CDCl$_3$) δ: ppm

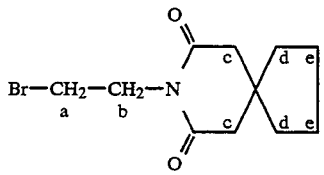

1.46 to 1.54, multiplet, 4H, 2 CH$_2$ 1.67 to 1.76, multiplet, 4H, 2 CH$_2$ 2.62, singlet, 4H, H$_c$ 3.48, triplet J=6.9 Hz, 2H, Ha 4.20, triplet J=6.9 Hz, 2H, Hb

PREPARATIONS 5 TO 7

By proceeding in the same way as in the case of preparation 1 but replacing 8-azospiro[4,5]decane-7,9- dione with:

1,1-dioxo-1,2-benzisothiazol-3(2H)-one, N-(4-bromobutyl)-1,1-dioxo-1,2-benzisothiazol-3(2H)-one is obtained in a yield of 60%.

Infrared (film): 1720 cm$^{-1}$ v C=O 1300 and 1170 cm$^{-1}$ v SO$_2$ $^1$H NMR 300 MHz (CDCl$_3$) δ: ppm

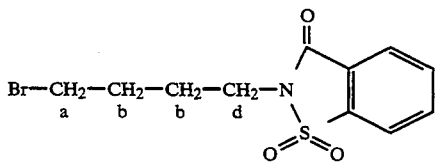

1.95 to 2.05, multiplet, 4H, Hb and Hc 3.44, triplet J=7.1 Hz, 2H, Ha 3.82, triplet J=7.1 Hz, 2H, Hd 7.78 to 8.05, multiplet, 4H aromatic 2,4-dioxo-3-azabicyclo[3.3.0]octane, N-(4-bromobutyl)-3-azabicyclo[3.3.0]octane-2,4-dione is obtained in a yield of 58%.

Infrared (film): 1685 and 1760cm$^{-1}$ v C=O $^1$H NMR 300 MHz (CDCl$_3$) δ: ppm

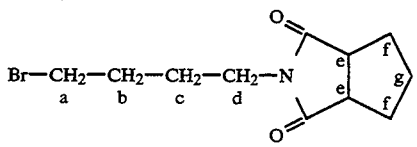

1.15 to 1.38, multiplet, 2H, CH$_2$ 1.62 to 2.14, multiplet, 8H, 4 CH$_2$ 3.08 to 3.17, multiplet, 2H, H$_e$ 3.38, triplet J=6.6 Hz, 2H, Ha 3.48, triplet J=6.6 Hz, 2H, Hd 4,4-dimethylpiperidine-2,6-dione, N-(4-bromobutyl)-4,4-dimethylpiperidine-2,6-dione is obtained in a yield of 65%.

Infrared (film): 1660 and 1715 cm$^{-1}$ v C=O $^1$H NMR 300 MHz (CDCl$_3$) δ: ppm

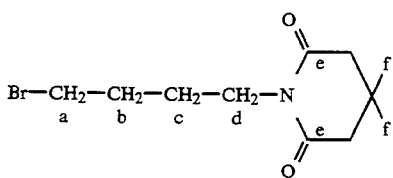

1.06, singlet, 6H, Hf 1.61 to 1.73, multiplet, 2H, CH₂ 1.80 to 1.91, multiplet, 2H, CH₂ 2.51, singlet, 4H, He 3.41, triplet J=6.3 Hz, 2H, Ha 3.80, triplet J=6.3 Hz, 2H, Hd

PREPARATIONS 8 AND 9

By proceeding in the same way as in the case of preparation 4, but replacing 1,2-dibromobutane with 1,4-dibromobutane and 8-azaspiro[4,5]decane-7,9-dione with:

3-azabicyclo[3.3.0]octan-2-one, N-(4-bromobutyl)-3-azabicyclo[3.3.0]octan-2-one is obtained in a yield of 52%.

Infrared (film): 1670 cm⁻¹ ν C=O

¹H NMR 300 MHz (CDCl₃) δ: ppm

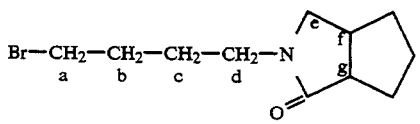

1.40 to 2.29, multiplet, 10H, 5CH₂ 2.70 to 2.95, multiplet, 2H, CH₂ 3.00, split doublet J₁=9.7 Hz J₂=2.6 Hz, Hf 3.20 to 3.40, multiplet, 2H, CH₂ 3.44, triplet J=6.5 Hz, 2H, Ha 3.58, triplet J=9.7 Hz, 1H, Hg oxazolo[4,5-b]pyridin-2(3H)-one, N-(4-bromobutyl)oxazolo[4,5-b]pyridin-2(3H)-one is obtained in a yield of 64%.

Infrared (film): 1775 cm⁻¹ ν C=O

¹H NMR 300 MHz (CDCl₃) δ: ppm

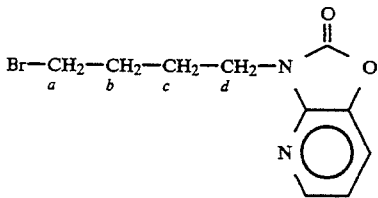

2.41 to 2.51, multiplet, 4H, Hb and Hc 3.47, triplet J=6.7 Hz, 2H, Ha 4.10, triplet J=6.7 Hz, 2H, Hd 7.08, split doublet J₁=8 Hz J₂=5.1 Hz, 1H, pyridine 7.41, doublet J=8 Hz, 1H, pyridine 8.11, doublet J=5.1 Hz, 1H, pyridine

PREPARATION 10:
N-[(3-BROMOPROPYL)OXY]-8-AZASPIRO[4,5]-DECANE-7,9-DIONE

This compound is prepared, in a yield of 68%, from 8-hydroxy-8-azaspiro[4,5]decane-7,9-dione using the method described by Nicholas J. Hrib et al. (J. Med. Chem. (1991) 34 1068).

Infrared (film): 1690 and 1740 cm⁻¹ ν C=O

¹H NMR 300 MHz (CDCl₃) δ: ppm

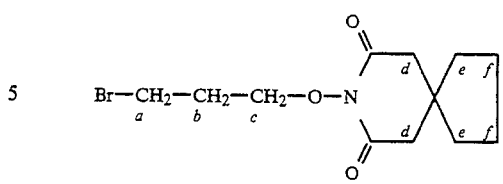

1.51 to 1.61, multiplet, 4H, 2 CH₂ 1.68 to 1.78, multiplet, 4H, CH₂ 2.21 to 2.28, multiplet, 2H, Hb 2.68, singlet, 4H, Hd 3.65, triplet J=6.3 Hz, 2H, Ha 4.12, triplet J=6.3 Hz, 2H, Hc

EXAMPLE 1:
SPIRO[(5-METHOXYCHROMAN)-3,2'-(PYRROLIDIN-5'- ONE)]

Stage I: Methyl 3-(5-Methoxy-3-Nitrochroman-3-Yl)-Propionate

Add 0.4 cm³ of benzyltrimethylammonium methylate and 5.16 cm³ of methyl acrylate to a solution of 4 g (0.019 mol) of 5-methoxy-3-nitrochroman in 60 cm³ of methanol.

The reaction mixture is stirred at 70° C. for 90 minutes and then cooled and concentrated at reduced pressure.

Add 30 cm³ of water and extract with methylene chloride.

The crude product obtained by removal of methylene chloride is purified by chromatography on a silica column (eluent: 50 methylene chloride/50 petroleum ether).

5.1 g (90%) of methyl 3-(5-methoxy-3-nitro- chroman-3-yl)propionate are thus obtained in the form of colorless oil.

Infrared (film): 1730 cm⁻¹ ν C=O

¹H NMR 300 MHz (CDCl₃) δ: ppm

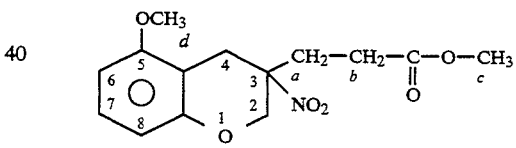

2.15 to 2.59, multiplet, 4H, Ha and Hb 2.91, doublet J=17.5 Hz, 1H, H₄ 3.57, doublet J=17.5 Hz, 1H, H₄ 3.68, singlet, 3H, Hc 3.84, singlet, 3H, Hd 4.10 and 4.57, 2 doublets J=11.6 Hz, 2H, H₂ 6.48 and 6.51, 2 doublets J=8.3 Hz, 2H, H aromatic 7.11, triplet J=8.3 Hz, 1H, H aromatic Stage II: Spiro[(5-Methoxychroman)-3,2'-(Pyrrolidin-5'-One)]

Heat a solution of 5.1 g (0.017 mol) of methyl 3-(5-methoxy-3-nitrochroman-3-yl)propionate in 100 cm³ of methanol at 60° C. for 20 hours under hydrogen atmosphere in the presence of 0.715 g of Raney nickel.

After removal of the catalyst by filtation, the methanolic solution is heated to reflux for 4 hours.

After cooling and drying, the crude product obtained is purified by chromatography on a silica column (eluent: 80 methylene chloride/20 methanol).

3.66 g (91%) of spiro[(5-methoxychroman)-3,2'- (pyrrolidin-5'-one)] are thus obtained in the form of a white solid.

Melting point: 210° C.

Infrared (KBr): 3250 cm⁻¹ ν NH 1670 cm⁻¹ ν C=O

¹H NMR 300 MHz (CDCl₃) δ: ppm

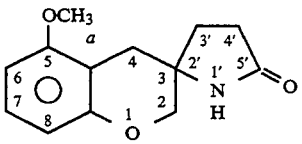

1.94 to 2.16, multiplet, 2H, H₃ 40 2.43 to 2.59, multiplet, 2H, H₄' 2.75 and 2.87, 2 doublets J=16.5 Hz, H₄ 3.83, singlet, 3H, Ha 3.89 and 3.94, 2 doublets J=11 Hz, H₂ 5.83, unresolved bands, 1H, NH 6.46 and 6.53, 2 doublets J=8.3 Hz, 2H, H aromatic 7.11, triplet J=8.3 Hz, 1H, H aromatic

EXAMPLE 2:
SPIRO[CHROMAN-3,2'-(PYRROLIDIN-5'-ONE)]

By proceeding as in Example 1 but replacing 5-methoxy-3-nitrochroman with 3-nitrochroman in stage I, spiro[chroman-3,2'-(pyrrolidin-5'-one)] is obtained in a yield of 96%.

Melting point: 179° C.
Infrared (KBr): 3225 cm⁻¹ ν NH 1675 cm⁻¹ ν C=O
¹H NMR 300 MHz (CDCl₃) δ: ppm

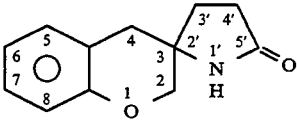

1.91 to 2.17, multiplet, 2H, H₃' 2.51, triplet J=8.2 Hz; 2H, H₄' 2.88 and 2.97, 2 doublets J=16.4 Hz, 2H, H₄ 3.94 and 3.98, 2 doublets J=10.3 Hz, 2H, H₂ 6.04, unresolved bands, 1H, NH 6.83 to 7.18, multiplet, 4H, H aromatic

EXAMPLE 3:
SPIRO[(5-METHOXYCHROMAN)-3,2'-(N-PROPYLPYRROLIDIN-5'-ONE)]

Add 1 g (4.29 mmol) of spiro[(5-methoxychroman)-3,2'-(pyrrolidin-5'-one)] in solution in 2 cm³ of DMF to a suspension of 0.113 g (4.71 mmol) of sodium hydride in 18 cm³ of DMF.

Stir at 60° C. for one hour and then add 3.61 g (0.021 mmol) of 1-iodopropane. Continue heating for 8 hours and then cool and remove the solvent at reduced pressure.

Add 10 cm³ of water and extract with methylene chloride.

The crude product obtained by drying the methylene chloride is purified by chromatography on a silica column (eluent: 50 ethyl ether/50 methylene chloride).

Spiro[(5-methoxychroman)-3,2'-(N-propylpyrrolidin-5'-one)] is thus obtained in the form of white crystals in a yield of 64%.

Melting point: 90° C.
Infrared (KBr): 1670 cm⁻¹ ν C=O
¹H NMR 300 MHz (CDCl₃) δ: ppm

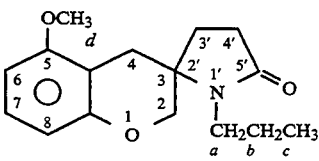

0.88, triplet J=8.5 Hz, 3H, Hc 1.50 to 1.66, multiplet, 2H, Hb 1.74 to 1.84 and 2.07 to 2.16, 2 multiplets, 2H, H₃' 2.44, triplet J=8.1 Hz, 2H, H₄' 2.69, pair of doublets J=17.1 Hz, J=2.4 Hz, 1H, H₄ 2.90, doublet J=17.1Hz, 1H, H₄ 3 to 3.23, multiplet, 2H, Ha 3.84, singlet, 3H, Hd 3.88, pair of doublets J=10.3 Hz, J=2.4 Hz, 1H, H₂ 3.97, doublet J=10.3 Hz, 1H, H₂ 6.48 and 6.52, 2 doublets J=8.3 Hz, 2H, H aromatic 7.11, triplet J=8.3 Hz, 1H, H aromatic

EXAMPLE 4:
SPIRO[(5-METHOXYCHROMAN)-3,2'-PYRROLIDINE]

Add 0.35 cm³ of borane-dimethyl sulfide complex (2M) to a solution of 0.1 g (0.42 mmol) of spiro[(5-methoxychroman)-3,2'-(pyrrolidin-5'-one)] in 5 cm³ of THF.

Heat the reaction mixture to reflux for 4 hours, dry under reduced pressure and take up the crude reaction product with 10 cm³ of 2M hydrochloric acid and 5 cm³ of methanol.

The solution is heated to reflux for 90 minutes and then made basic with a 2M aqueous sodium hydroxide solution and extracted with methylene chloride.

After drying, the methylene chloride phase is dried and the crude product purified by chromatography on a silica column (eluent: 95 methylene chloride/5 methanol).

70 mg (76%) of spiro[(5-methoxychroman)-3,2'-pyrrolidine] are obtained in the form of oil.

Infrared (film): 3300 cm⁻¹ ν NH 1585 cm⁻¹ ν C=C aromatic
¹H NMR 300 MHz (CDCl₃) δ: ppm

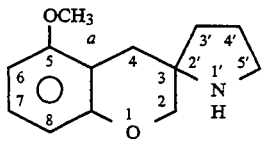

1.56 to 1.95, multiplet, 4H, H₄' and H₃' 2.21, singlet, 1H, NH 2.68, singlet, 2H, H₄ 2.96 to 3.17, multiplet, 2H, H₅' 3.80, singlet, 3H, Ha 3.82, singlet, 2H, H₂ 6.43 and 6.52, 2 doublets J=8.3 Hz, 2H, H aromatic 7.06, triplet J=8.3 Hz, 1H, H aromatic

EXAMPLE 5:
SPIRO[(5-METHOXYCHROMAN)-3,2'-(N-PROPYLPYRROLIDINE)]

Add 0.23 g (1.37 mmol) of 1-iodopropane and 0.19 g (1.37 mmol) of potassium carbonate to a solution of 0.1 g (0.456 mmol) of spiro[(5-methoxychroman)-3,2'- pyrrolidine].

Heat to 60° C. for 3 hours, cool, remove the solvent at reduced pressure, hydrolyze and extract the aqueous phase with methylene chloride.

After drying, the crude product obtained is purified by chromatography on a silica column (eluent: 20 ethyl ether/80 petroleum ether).

Spiro[(5-methoxychroman)-3,2'-(N-propylpyrrolidine)] is thus obtained in a yield of 84%.

Melting point (oxalate): 62° C.
Infrared (film): 2960 to 2800 cm⁻¹ ν CH 1585 cm⁻¹ ν C=C aromatic
¹H NMR 300 MHz (CDCl₃) δ: ppm

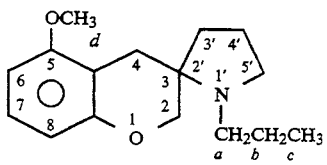

0.90, triplet, J=7.4 Hz, 3H, Hc 1.42 to 1.97, multiplet, 6H, H$_3'$, H$_4'$, H$_b$ 2.38 to 2.61, multiplet, 3H, H$_a$, H$_4$ 2.70, doublet J=17 Hz, 1H, H$_4$ 2.82 to 3.03, multiplet, 2H, H$_5'$ 3.78, doublet J=10.3 Hz , 1H, H$_2$ 3.81, singlet, 3H, H$_d$ 3.83, doublet J=10.3 Hz, 1H, H$_2$ 6.42 and 6.48, 2 doublets J=8.3 Hz, 2H, H aromatic 7.06, triplet J=8.3 Hz, 1H, H aromatic

EXAMPLE 6:
SPIRO[CHROMAN-3,2'-(N-PROPYLPYRROLIDINE)]

By proceeding as in Example 5 but replacing spiro[(5-methoxychroman-3,2'-pyrrolidine] with spiro[chroman-3,2'-(N-propylpyrrolidine)], spiro[chroman-3,2'-(N-propylpyrrolidine)] is obtained in a yield of 61%.

Melting point (oxalate): 48° C.

Infrared (film): 2800 to 2980 cm$^{-1}$ ν CH 1575 cm$^{-1}$ ν C=C aromatic $^1$H NMR 300 MHz (CDCl$_3$) δ: ppm

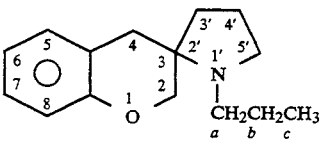

0.91, triplet, J=7.4 Hz, 3H, H$_c$ 1.43 to 2.01, multiplet, 6H, H$_b$, H$_3'$, H$_4'$ 2.39 to 2.59, multiplet, 3H, H$_a$, H$_4$ 2.83 to 2.96, multiplet, 2H, H$_5'$ 3.02, doublet J=16.1 Hz, 1H, H$_4$ 3.83, pair of doublets J=10.3 Hz J=2.4 Hz, 1H, H$_2$ 3.88, doublet J=10.3 Hz, 1H, H$_2$ 6.78 to 7.11, multiplet, 4H, H aromatic

EXAMPLE 7:
SPIRO[(5-HYDROXYCHROMAN)-3,2'-(N-PROPYLPYRROLIDINE)]

Add 11 cm$^3$ of hydrobromic acid at a concentration of 48% in water to a solution of 1.1 g (4.2 mmol) of spiro[(5-methoxychroman)-3,2'-(N-propylpyrrolidine)] in 22 cm$^3$ of acetic acid.

The reaction mixture is heated to reflux for 5 hours and then cooled, dried at reduced pressure, taken up with 40 cm$^3$ of a saturated aqueous solution of sodium bicarbonate and extracted with methylene chloride.

The crude product obtained by drying the methylene chloride is purified by chromatography on a silica column (eluent: 50 ethyl ether/50 petroleum ether).

0.91 g (88%) of spiro[(5-hydroxychroman)-3,2'-(N-propylpyrrolidine)] are thus obtained.

Melting point (base): 185°–186° C.

Melting point (oxalate salt): 98° C. Infrared (KBr): 3250 cm$^{-1}$ (broad band) ν OH $^1$H NMR 300 MHz (DMSO-d$_6$) δ: ppm

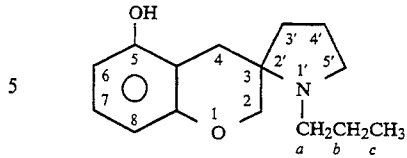

0.83, triplet, J=7.4 Hz, 3H, H$_c$ 1.30 to 1.45, multiplet, 3H, H$_b$, H$_3'$ 1.65 to 1.80, multiplet, 3H, H$_3'$, H$_4'$ 2.32, doublet J=17 Hz, 1H, H$_4$ 2.39 to 2.53, multiplet, 2H, H$_a$ 2.59, doublet J=17 Hz, 1H, H$_4$ 2.71 to 2.90, multiplet, 2H, H$_5'$ 3.69 and 3.76, 2 doublets J=10.3 Hz, 2H, H$_2$ 6.21 and 6.32, 2 doublets J=8.3 Hz, 2H, H aromatic 6.81, triplet J=8.3 Hz, 1H, H aromatic 9.32, singlet, 1H, OH

EXAMPLE 8:
SPIRO[(5-METHOXYCHROMAN)-3,2'-{N-[4'-(8'-AZASPIRO[4',5']DECANE-7',9'-DION-8'-YL)-n-BUT-1'-YL]PYRROLIDINE}]

Add 1.82 g (6.02 mmol) of N-(4-bromobut-1-yl)-8-azaspiro[4,5]decane-7,9-dione, 1.66 g (16.41 mmol) of triethylamine and a catalytic quantity of potassium iodide to a solution of 1.2 g (5.47 mmol) of spiro[(5-methoxychroman)-3,2'-pyrrolidine] in 10 cm$^3$ of N,N-dimethylformamide.

The reaction mixture is heated to 60° C. for 8 hours, then cooled, concentrated at reduced pressure, taken up with 10 cm$^3$ of water and extracted with methylene chloride.

The residual oil obtained by drying is purified by chromatography on a silica column (eluent: 50 methylene chloride/50 ethyl ether).

1.3 g (54%) of spiro[(5-methoxychroman)-3,2'-{N-[4'-(8'-azaspiro[4',5']decane-7',9'-dion-8'-yl)-n-but-1'-yl]pyrrolidine}] are thus obtained.

Melting point (oxalate): 68° C.

Infrared (film): 1665 and 1720 cm$^{-1}$ ν C=O $^1$H NMR 300 MHz (CDCl$_3$) δ: ppm

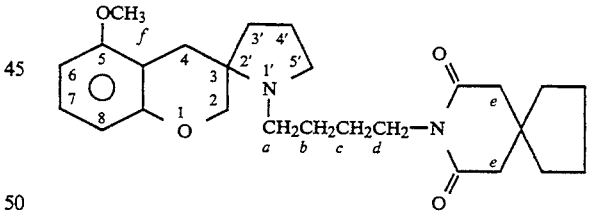

1.35 to 1.95, multiplet, 16H, 8 CH$_2$ 2.40 to 2.56, multiplet, 3H, H$_4$and H$_a$ 2.57, singlet, 4H, H$_e$ 2.66, doublet J=16.8 Hz, 1H, H$_4$ 2.76 to 3.03, multiplet, 2H, H$_5'$ 3.69 to 3.79, multiplet, 4H, H$_d$ and H$_2$ 3.81, singlet, 3H, H$_f$ 6.41 and 6.46, 2 doublets J=8.3 Hz, 2H, aromatic 7.04, triplet J=8.3 Hz, 1H, H aromatic

EXAMPLE 9:
SPIRO[CHROMAN-3,2'-{N-[4'-(8'-AZASPIRO[4',5']DECANE-7',9'-DION-8'-YL)-n-BUT-1'-YL]PYRROLIDINE}]

By proceeding as in Example 8, but replacing spiro[(5-methoxychroman)-3,2'-pyrrolidine] with spiro[chroman-3,2'-pyrrolidine], spiro [chroman-3,2'-{N-[4'-(8'-azaspiro[4',5']decane-7',9'-dion-8'-yl)-n-but-1'-yl]pyrrolidine}] is obtained in a yield of 55%.

Melting point (oxalate): 66° C.

Infrared (film): 1715 and 1660 cm$^{-1}$ v C=O
$^1$H NMR 300 MHz (CDCl$_3$) δ: ppm

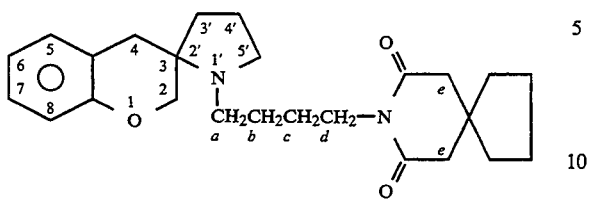

1.40 to 2, multiplet, 16H, 8 CH$_2$ 2.44, doublet J=16.1 Hz, 1H, H$_4$ 2.48 to 2.56, multiplet, 2H, Ha 2.58, singlet, 4H, He 2.79 to 2.96, multiplet, 2H, H$_5'$ 3.0, doublet J=16.1 Hz, 1H, H$_4$ 3.73 to 3.91, multiplet, 4H, H$_2$and Hd 6.77 to 7.10, multiplet, 4H, H aromatic

EXAMPLE 10:
SPIRO[{5-[4-(8-AZASPIRO[4,5]DECANE-7,9-DION-8-YL)-n-BUT-1-YL]OXYCHROMAN}-3,2'-(N- PROPYLPYRROLIDINE)]

Add 0.076 g (0.25 mmol) of N-(4-bromobut-1-yl)-8-azaspiro[4,5]decane-7,9-dione, 0.095 g (0.69 mmol) of potassium carbonate and a catalytic quantity of potassium iodide to a solution of 0.058 g (0.23 mmol) of spiro-[(5-hydroxychroman)-3,2'-(N-propylpyrrolidine)] in 3 cm$^3$ of N,N-dimethylformamide.

Heat to 60° C. for 2 hours, cool, concentrate at reduced pressure and then take up the crude reaction product in 10 cm$^3$ of water and extract with methylene chloride.

The crude oil obtained is purified by chromatography on a silica column (eluent: 50 ethyl ether/50 methylene chloride). Spiro [{5-[4-(8-azaspiro[4,5]decane-7,9-dion-8- yl)-n-but-1-yl]oxychroman}-3,2'-(N-propylpyrrolidine)] is thus obtained in the form of oil in a yield of 79%.

Melting point (oxalate): 68° C.
Infrared (film): 1660 and 1715 cm$^{-1}$v C=O
$^1$H NMR 300 MHz (CDCl$_3$) δ: ppm

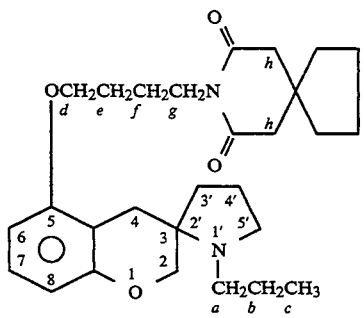

0.94, triplet J=7.4 Hz, 3H, H$_c$ 1.48 to 2.03, multiplet, 18H, 9 CH$_2$ 2.40 to 2.68, multiplet, 7H, H$_h$, H$_4$ and H$_a$ 2.74, doublet J=17 Hz, 1H, H$_4$ 2.90 to 3.06, multiplet, 2H, H$_5'$ 3.82 to 3.92, multiplet, 4H, H$_g$ and H$_2$ 3.95 to 4.04, multiplet, 2H, H$_d$ 6.41 and 6.48, 2 doublets J=8.3 Hz, 2H, H aromatic 7.04, triplet J=8.3 Hz, 1H, H aromatic

EXAMPLES 11 AND 12

By proceeding in the same way as in Example 10 but replacing N-(4-bromo-n-but-1-yl)-8-azaspiro[4,5]-decane-7,9-dione with:

N-(4-bromo-n-but-1-yl)-4,4-dimethylpiperidine-2,6-dione, spiro[{5-[4-(4,4-dimethylpiperidine-2,6-dione-1-yl)-n-but-1yl]oxychroman}-3,2'-(N-propyl- pyrrolidine)] is obtained

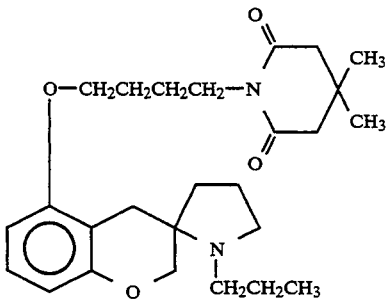

N-(4-bromo-n-but-1-yl)-3-azabicyclo[3.3.0]octane-2,4-dione, spiro[{5-[4-(3-azabicyclo[3.3.0]octane-2,4-dione-3-yl)-n-but-1-yl]oxychroman}-3,2'-(N-propylpyrrolidine)] is obtained.

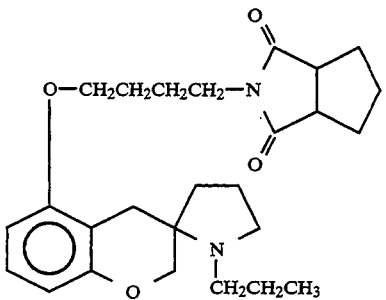

EXAMPLES 13 TO 32

By proceeding in the same way as in Example 8, but replacing N-(4-bromobut-1-yl)-8-azaspiro[4,5]decane-7,9-dione with:

N-(4-bromobutyl)phthalimide, spiro[(5-methoxychroman)-3,2'-[N-(4'-phthalimido-n-but-1'- yl)pyrrolidine]] is obtained

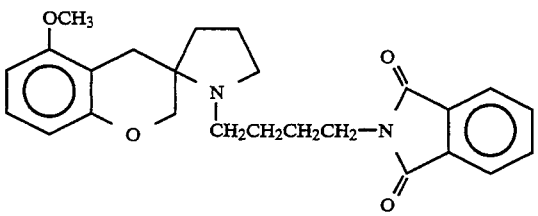

Infrared (film): 1700 cm$^{-1}$ v C=O

N-(3-bromopropyl)phthalimide, spiro[(5-methoxychroman)-3,2'-[N-(3'-phthalimidoprop-1'-yl)pyrrolidine]] is obtained N-(3-bromoprop-1-yl)-8-azaspiro[4,5]decane-7,9- dione, spiro [(5-methoxychroman)-3,2'-{N-[3'-(8'-azaspiro[4',5']decane-7',9'-dion-8'-yl)-n-prop-1'-yl]pyrrolidine}] is obtained

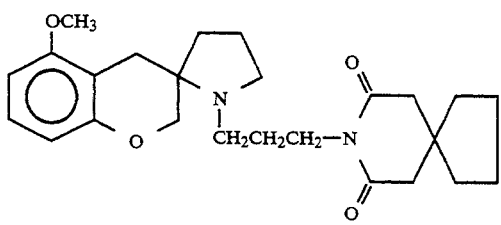

N-(5-bromopent-1-yl)-8-azaspiro[4,5]decane-7,9-dione, spiro[(5-methoxychroman)-3,2'-{N-[5'-(8'-azaspiro-[4,',5']decane-7',9'-dion-8'-yl)-n-pent-1'-yl]pyrrolidine}] is obtained

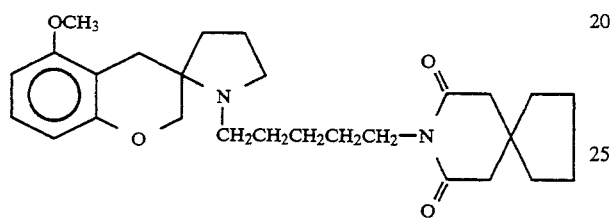

N-(2-bromoethyl)-8-azaspiro[4,5]decane-7,9-dione, spiro[(5-methoxychroman)-3,2'-{N-[2'-(8'-azaspiro[4',5']decane-7',9'-dion-8'-yl)-ethyl]pyrrolidine}] is obtained

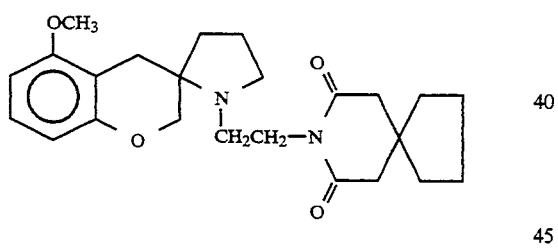

N-[(3-bromopropyl)oxy]-8-azaspiro[4,5]decane-7,9-dione, spiro [(5-methoxychroman)-3,2'-{N-[3'-(8'-azaspiro[4',5']decane-7',9'-dion-8'-yl)oxy-n-prop-1-yl]pyrrolidine}] is obtained

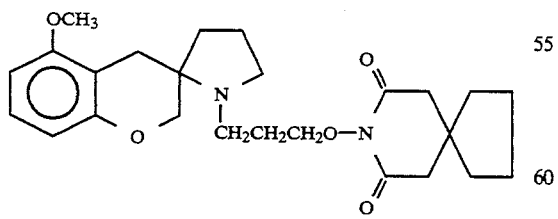

N-(4-bromobutyl)oxazolo[4,5-b]pyridin-2(3H)-one, spiro[(5-methoxychroman)-3,2'-{N-[4'-(oxazolo[4',5'-b]pyridin-2'(3H)-on-3'-yl)-n-but-1'-yl]pyrrolidine}] is obtained

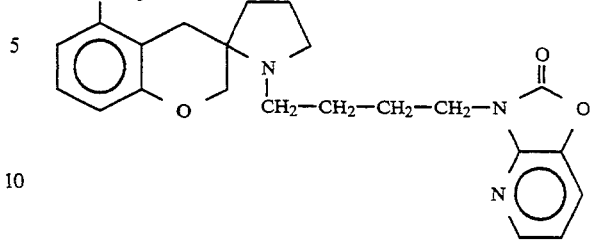

N-(4-bromobutyl)oxazolo[5,4-b]pyridin-2(3H)-one, spiro[(5-methoxychroman)-3,2'-{N-[4'-(oxazolo[5',4'-b]pyridin-2'(3H)-on-3'-yl)-n-but-1'-yl]pyrrolidine}] is obtained

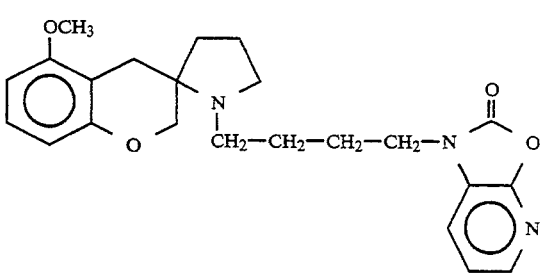

N-(4-bromobutyl)-3-azabicyclo [3.3.0]octane-2,4-dione, spiro[(5-methoxychroman)-3,2'-{N-[4'-(3'-azabicyclo[3.3.0]octane-2,4-dion-3-yl)-n-but-1'-yl]pyrrolidine}] is obtained

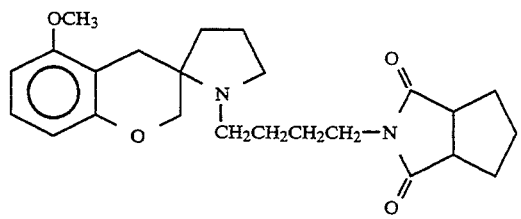

N-(4-bromobutyl)-4,4-dimethylpiperidine-2,6-dione, spiro [(5-methoxychroman)-3,2'-{N-[4'-(4',4'-dimethylpiperidine-2',6'-dion-1'-yl)-n-but-1'-yl]-pyrrolidine}] is obtained

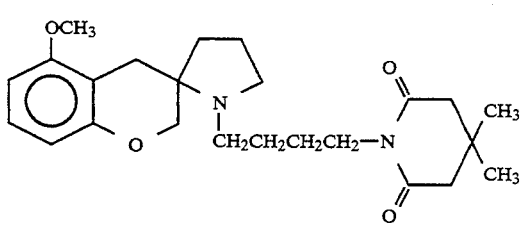

N-(4-bromobutyl)benzoxazolin-2-one, spiro[(5-methoxychroman)-3,2'-{N-[4'-(benzoxazolin-2'-on-3'-yl)-n-but-1'-yl]pyrrolidine}] is obtained

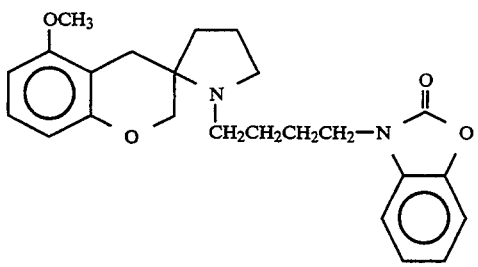

N-(4-bromobutyl)-1,1-dioxo-1,2-benzisothiazol-3(2H)- one, spiro[(5'methoxychroman)-3,2'-{N-[4'-(1',1'- dioxo-1',2'-benzisothiazol-3'(2H)-on-2'-yl)-n-but- 1'-yl]pyrrolidine}] is obtained

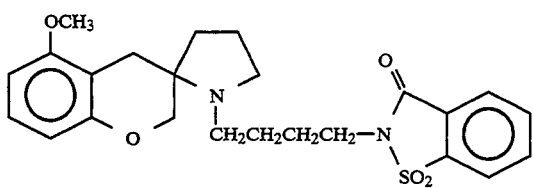

N-(4-bromobutyl)-3-azabicyclo[3.3.0]octan-2-one, spiro[(5-methoxychroman)-3,2'-{N-[4'-(3'-azabicyclo[3.3.0]octan-2'-on-3'-yl)-n-but-1'-yl]pyrrolidine}] is obtained

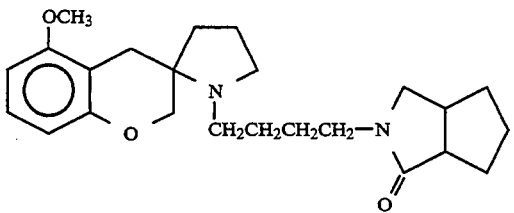

N-(4-bromobut-1-yl)piperidin-2-one, spiro[(5-methoxychroman)-3,2'-{N-[4'-(piperidin-2'-on-1'-yl)-n-but-1'-yl]pyrrolidine}] is obtained

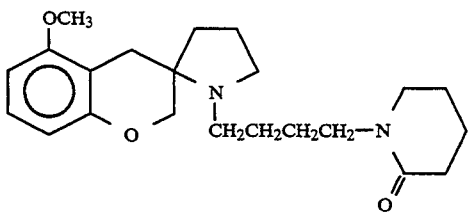

benzyl bromide, spiro [(5-methoxychroman)-3,2'-(N-benzylpyrrolidine)] is obtained

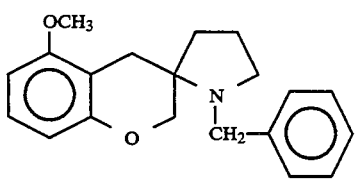

3,4-difluorobenzyl bromide, spiro[(5-methoxychroman)-3,2'-[N-(3',4'-difluorobenzyl)pyrrolidine]] is obtained 4-trifluoromethylbenzyl bromide, spiro[(5-methoxychroman)-3,2'-[N-(4'-trifluoromethylbenzyl)pyrrolidine]] is obtained 4-methylbenzyl bromide, spiro[(5-methoxychroman)-3,2'-[N-(4'-methylbenzyl)pyrrolidine]] is obtained phenethyl bromide, spiro[(5-methoxychroman)-3,2'-(N-phenethylpyrrolidine)] is obtained 3-bromopropylbenzene, spiro[(5-methoxychroman)-3,2'- [N-(3'-phenyl-n-prop-1'-yl)pyrrolidine]] is obtained.

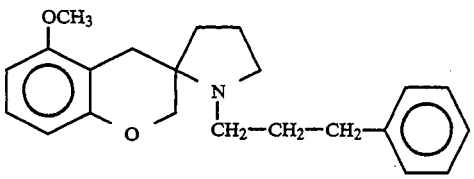

EXAMPLE 33:
SPIRO[(5-METHOXYCHROMAN)-3,2'-[N-(2'-AMINOETHYL)PYRROLIDINE]]

Stage I:
Spiro[(5-Methoxychroman)-3,2'-(N-Cyanomethylpyrrolidine)]

Add 0.905 g (12 mmol) of chloroacetonitrile, 1.66 g (12 mmol) of potassium carbonate and a catalytic quantity of potassium iodide to a solution of 0.89 g (4.05 mmol) of spiro[(5-methoxychroman)-3,2'-pyrrolidine].

Heat to 60° C. for 20 hours then cool, concentrate at reduced pressure, take up with water and then extract with methylene chloride.

The crude product obtained after drying the methylene chloride phase is purified by chromatography on a silica column (eluent: 99 methylene chloride/1 methanol).

Spiro[(5-methoxychroman)-3,2'-(N-cyanomethylpyrrolidine)] is thus obtained in a yield of 75%.

Stage II:
Spiro[(5-Methoxychroman)-3,2'-[N-(2'-Aminoethyl)-pyrrolidine]]

Slowly add 5.6 mmol of LiAlH$_4$ to a solution, under argon atmosphere, of 0.72 g (2.8 mmol) of spiro[(5-methoxychroman)3,2'-(N-cyanomethylpyrrolidine)] in 20 cm$^3$ of tetrahydrofuran.

Stir at room temperature for 30 minutes then cool with ice and hydrolyze with 7 cm$^3$ of iced water.

The organic phase is separated off, dried, and the crude product obtained purified by chromatography on a silica column (eluent: 99 methylene chloride/1 methanol).

Spiro[(5-methoxychroman)-3,2'-[N-(2'-aminoethyl) pyrrolidine]] is thus obtained in a yield of 70%.

1NMR 300 MHz (CDCl$_3$) δ: ppm

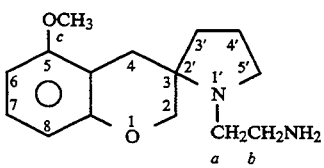

1.45 to 1.90, multiplet, 4H, H$_3$' and H$_4$' 2.41 to 2.75, multiplet, 6H, H$_4$, H$_a$, H$_b$ 2.95, multiplet, 2H, H$_5$' 3,80 to 3.85, multiplet singlet, 7H, H$_c$, H$_2$ and NH$_2$ 6.40 and 6.5, 2 doublets J=8 Hz, 2H, H aromatic 7.05, triplet J=8 Hz, 1H, H aromatic

EXAMPLE 34:
SPIRO[(5-METHOXYCHROMAN)-3,2'-[N-(4'-AMINO-n-BUT-1-YL)PYRROLIDINE]]

Stage I: Spiro[(5-Methoxychroman)-3,2'-[N-(3'-Cyano-n-Prop-1'-yl)pyrrolidine]]

By proceeding as in Example 33 stage I but replacing chloroacetonitrile with 4-bromobutyronitrile, spiro[(5-methoxychroman)-3,2'-[N-(3'-cyano-n-prop-1'-yl)pyrrolidine]] is obtained.

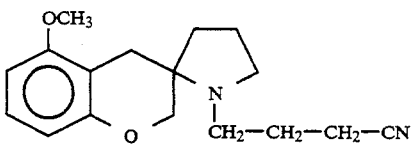

Stage II:
Spiro[(5-Methoxychroman)-3,2'-[N-(4'-Amino-n-But-1'-yl)pyrrolidine]]

By reducing spiro[(5-methoxychroman)-3,2'-[N-(3-cyano-n-prop-1-yl)pyrrolidine ]] under the conditions of Example 33 stage II, spiro[(5-methoxychroman)-3,2'-[N- (4'-amino-n-but-1'-yl)pyrrolidine]] is obtained.

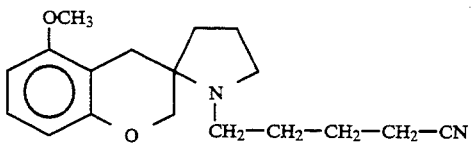

EXAMPLE 35:
SPIRO[(5-METHOXYCHROMAN)-3,2'-[N-(2'-para-TOLUENESULFONYLAMINOETHYL)PYRROLIDINE]]

Add dropwise 1.2 g (11.4 mmol) of triethylamine and then 0.8 g (5.8 mmol) of tosyl chloride in solution in methylene chloride to a solution of 1 g (3.8 mmol) of-spiro[(5-methoxychroman)-3,2'-[N-(2'-aminoethyl)pyrrolidine]] in 30 cm³ of methylene chloride at 0° C.

After 30 minutes' stirring at room temperature the solvent is removed and the crude product obtained purified by chromatography on a silica column (eluent: methylene chloride).

Spiro[(5-methoxychroman)-3,2'-[N- (2'-paratoluenesulfonylaminoethyl)pyrrolidine]] is thus obtained in a yield of 75%.

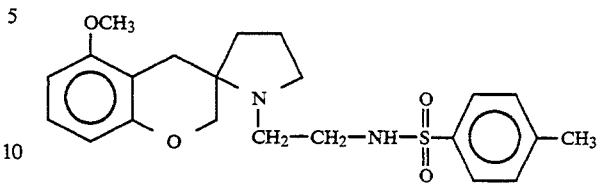

Infrared (KBr): 1150 cm⁻¹ v SO₂

EXAMPLE 36
:SPIRO[(5-METHOXYCHROMAN)-3,2'-[N-(4'-para-TOLUENESULFONYLAMINO-n-BUT-1'-YL)PYRROLIDINE]]

By proceeding as in Example 35 but replacing spiro[(5-methoxychroman)-3,2'-[N-(2'-aminoethyl)pyrrolidine]] with spiro[(5-methoxychroman)-3,2'-[N-(4'-amino- n-but-1'-yl)pyrrolidine]], spiro[(5-methoxychroman)-3,2'- [N-(4'-paratoluenesulfonylamino-n-but-1'-yl)pyrrolidine]] is obtained.

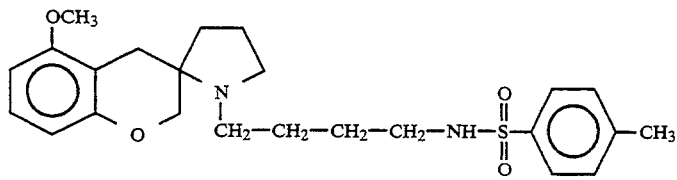

Infrared (KBr): 1150 cm⁻¹ v SO₂

EXAMPLE 37 to 42

By proceeding in the same way as in Example 36 but replacing tosyl chloride with:
4-iodobenzoyl chloride, spiro[(5-methoxychroman)-3,2'-{N-[4'-(4'-iodobenzamido)-n-but-1'-yl]pyrrolidine}] is obtained

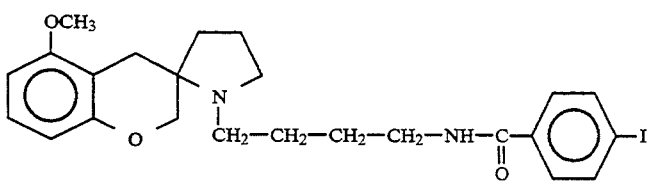

Infrared: 1620 cm⁻¹ v C=O
4-fluorobenzoyl chloride, spiro[(5-methoxychroman)- 3,2'-{N-[4'-(4'-fluorobenzamido)-n-but-1'-yl]pyrrolidine}] is obtained
Infrared: 1630 cm⁻¹ v C=O
2-methoxybenzoyl chloride, spiro[(5-methoxychroman)- 3,2'-{N-[4'-(2'-methoxybenzamido)-n-but-1'- yl]pyrrolidine}] is obtained
Infrared: 1635 cm⁻¹ v C=O
butanoyl chloride, spiro[(5-methoxychroman)-3,2'-[N-(4'-butyramido-n-but-1'-yl)pyrrolidine]] is obtained
3-phenylpropionyl chloride, spiro[(5-methoxychroman)-3,2'-{N-[4'-(3'-phenylpropionamido)-n-but- 1'-yl]pyrrolidine}] is obtained
3,4-dimethoxyphenylacetyl chloride, spiro[(5- methoxychroman)-3,2'-{N-[4'-(3',4'-dimethoxyphenyl-acetamido)-n-but-1'-yl]pyrrolidine}] is obtained.

EXAMPLE 43: SPIRO[(5-METHOXYCHROMAN)-3,2'-(N-ACETYLPYRROLIDINE)]

Add 0.253 g (2.51 mmol) of triethylamine, then, dropwise, 0.256 g (2.51 mmol) of acetic anhydride to a solution of 0.5 g (2.28 mmol) of spiro[(5-methoxychroman)-3,2'-pyrrolidine] in 10 cm³ of methylene chloride.

Stir at room temperature for 30 minutes, then concentrate at reduced pressure, take up the crude product with 10 cm³ of water and extract with methylene chloride.

The crude oil obtained is purified by chromatography on a silica column (eluent: ethyl acetate).

0.57 g (96%) of spiro[(5-methoxychroman)-3,2'- N-acetylpyrrolidine)] are thus obtained in the form of a white solid.

Melting point: 121° C.
Infrared (KBr): 1640 cm⁻¹ v C=O
¹H NMR 300 MHz (CDCl₃) δ: ppm

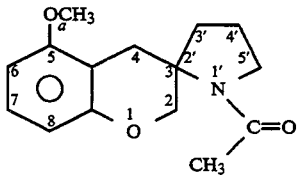

1.78 to 2.04, multiplet, 4H, H₃' and H₄' 2.06, singlet, 3H, H₆ 2.52, pair of doublets J=16.6 Hz, J=2.6 Hz, 1H, H₄ 3.50 to 3.63, multiplet, 2H, H₅' 3.67, doublet J=16.6 Hz, 1H, H₄ 3.76, pair of doublets J=10.2 Hz, J=2.6 Hz, 1H, H₂ 3.80, singlet, 3H, Hₐ 4.96, doublet J=10.2 Hz, 1H, H₂ 6.42 and 6.50, 2 doublets J=8.3 Hz, 2H, H aromatic 7.06, triplet J=8.3 Hz, 1 H, H aromatic

EXAMPLE 44: SPIRO[(5-METHOXYCHROMAN)-3,2'-(N-BENZOYLPYRROLIDINE)]

By proceeding in the same way as in Example 35, but replacing tosyl chloride with benzoyl chloride and spiro[(5-methoxychroman)-3,2'-[N-(2'-aminoethyl)pyrrolidine]] with spiro[(5-methoxychroman)-3,2'-pyrrolidine)], spiro [(5-methoxychroman)-3,2'-(N-benzoylpyrrolidine)] is obtained.

EXAMPLES 45 to 51

By proceeding in the same way as in Example 44 but replacing benzoyl chloride with:

4-methoxybenzoyl chloride, spiro[(5-methoxychroman)- 3,2'-[N-(4'-methoxybenzoyl)pyrrolidine]] is obtained 4-iodobenzoyl chloride, spiro[(5-methoxychroman)-3,2'-[N-(4'-iodobenzoyl)pyrrolidine]] is obtained 3-trifluoromethylbenzoyl chloride, spiro[(5-methoxychroman)-3,2'-[N-(3'-trifluoromethylbenzoyl)pyrrolidine]] is obtained 4-methylbenzoyl chloride, spiro[(5-methoxychroman)- 3,2'-[N-(4'-methylbenzoyl)pyrrolidine]] is obtained butyryl chloride, spiro[(5-methoxychroman)-3,2'-[N-butyrylpyrrolidine)] is obtained 3-phenylpropionyl chloride, spiro[(5-methoxychroman)-3,2'-[N-(3'-phenylpropionyl)pyrrolidine]] is obtained 3,4-dimethoxyphenylacetyl chloride, spiro[(5- methoxychroman)-3,2'-[N-(3',4'-dimethoxyphenylacetyl)pyrrolidine ]] is obtained.

EXAMPLES 52 to 53

By proceeding in the same way as in Example 4 but replacing spiro[(5-methoxychroman)-3,2'-(pyrrolidin-5'- one)] with:

spiro[(5-methoxychroman)-3,2'-[N-(4'-butyramido-n-but-1'-yl)pyrrolidine]], spiro[(5-methoxychroman)- 3,2'-{N-[4-(N-n-but-1-yl)amino-n-but-1-yl]pyrrolidine}] is obtained

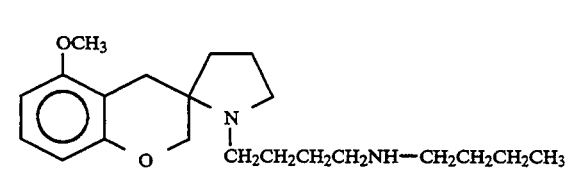

spiro[(5-methoxychroman)-3,2'-(N-[4-(3,4-dimethoxyphenylacetamido)-n-but-1-yl ]pyrrolidine}], spiro- [(5-methoxychroman)-3,2'-{N-[4'-(3',4'-dimethoxy- phenethyl)amino-n-but-1'-yl ]pyrrolidine}] is obtained.

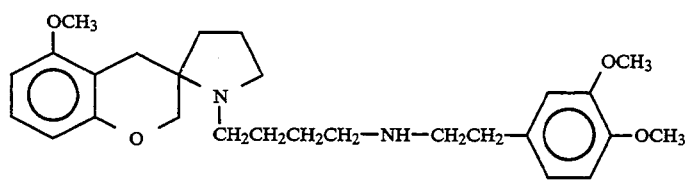

EXAMPLE 54: SPIRO[(5-ACETYLCHROMAN)-3,2'-(N-PROPYLPYRROLIDINE)]

Stage I:
Spiro[(5-Trifluoromethylsulfonyloxychroman)-3,2'-(N-propylpyrrolidine)]

Dissolve 1 g (4.04 mmol) of spiro[(5-methoxychroman)-3,2'-(N-propylpyrrolidine)] in 25 cm³ of methylene chloride and then add 1.62 cm³ of pyridine.

Cool to 0° C. then add dropwise 0.80 cm³ of trifluoromethanesulfonic anhydride.

Continue stirring at between 0° and +5° C. for 1 hour, then extract with methylene chloride, dry the organic phase and concentrate at reduced pressure.

The crude product is purified by chromatography on a silica column (eluent: ethyl acetate).

Spiro[(5-trifluoromethylsulfonyloxychroman)-3,2'-[N-propylpyrrolidine)] is thus obtained in a yield of 80%.

Infrared: 1405 cm⁻¹ and 1200 cm⁻¹ v sulfonate

Stage II:
Spiro[(5-Acetylchroman)-3,2'-(N-Propylpyrrolidine)]

Dissolve 0.8 g (2.11 mmol) of spiro[(5-trifluoromethylsulfonyloxychroman)-3,2'-(N-propylpyrrolidine)] in 8 cm³ of N,N-dimethylformamide.

Next add 0.43 g (4.22 mmol) of triethylamine, 1.16 g (11.61 mmol) of butyl vinyl ether, 0.023 g (0.058 mmol) of 1,2-bis(diphenylphosphino)ethane and 0.012 g (0.052 mmol) of Pd(OAc)₂, then heat to reflux for 8 hours.

After cooling, hydrolyze with 7 cm³ of 10N hydrochloric acid, stir at room temperature for one hour and extract with methylene chloride.

After drying at reduced pressure, the crude product is purified by chromatography on a silica column (eluent: ethyl ether/petroleum ether mixture gradient).

Spiro[(5-acetylchroman)-3,2'-(N-propylpyrrolidine)] is thus obtained in a yield of 40%.

Infrared: ν C═O

EXAMPLE 55: SPIRO [(5-METHOXYCHROMAN)-3,2'-(3'-METHYLPYRROLIDIN-5'-ONE)]

By proceeding in the same way as in Example 1 but replacing methyl acrylate in stage I with methyl crotonate, spiro[(5-methoxychroman)-3,2'-(3'-methyl-pyrrolidin-5'-one)] is obtained.

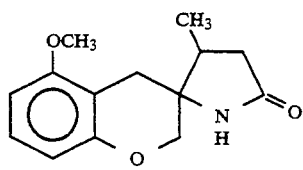

Infrared (KBr) 1665 cm⁻¹ ν C═O

EXAMPLE 56 SPIRO [(5-METHOXYCHROMAN)-3,2'-(3'-METHYL-N-PROPYLPYRROLIDINE)]

By reducing spiro[(5-methoxychroman)-3,2'-(3'-methylpyrrolidin-5'-one)] with borane-dimethyl sulfide according to Example 4 and then alkylating the spiro[(5-methoxychroman)-3,2'-( 3'-methylpyrrolidine)] thus obtained with 1-iodopropane according to Example 5, spiro[(5-methoxychroman)-3,2'-(3'-methyl-N-propylpyrrolidine)] is obtained.

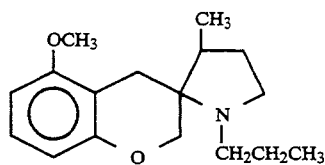

Infrared (film): 2970 to 2810 cm⁻¹ ν CH 1580 cm⁻¹ν C═C aromatic.

EXAMPLE 57: LEVOROTATORY ISOMER OF SPIRO[(5-METHOXY-CHROMAN)-3,2'-PYRROLIDINE]

Dissolve 1.41 g (4.05 mmol) of binaphthylphosphoric acid ((R)-(-)BNPPA) in 50 cm³ of a 90 methanol/10 methylene chloride mixture.

Add dropwise a solution of 1.27 g (5.79 mmol) of spiro[(5-methoxychroman)-3,2'-pyrrolidine] in 6 cm³ of methanol.

Stir at room temperature for 3 hours, then dry.

The crude salt obtained is recrystallized once first from acetonitrile and then three times from ethanol. 580 mg (35%) of binaphthylphosphate of the levorotatory isomer of spiro[(5-methoxychroman)-3,2'- pyrrolidine)] are obtained.

550 mg (0.97 mmol) of this salt are taken up in a mixture consisting of 10 cm³ of an aqueous solution (2M) of aqueous ammonia and 5 cm³ of ethyl acetate.

After stirring at room temperature for one hour, extract the amine with ethyl acetate and then, after drying, filter it on silica (eluent: ethyl acetate).

212 mg of the levorotatory isomer of spiro[(5-methoxychroman)-3,2'-pyrrolidine] are thus obtained.

Separation efficiency: 35%
Enantiomeric purity: 99.7%
Pouvoir rotatoire [α]_D^{20}= −15° (22 mg dans 3 cm³ de chloroforme)

EXAMPLE 58: DEXTROROTATORY ISOMER OF SPIRO[(5-METHOXYCHROMAN)-3,2'-PYRROLIDINE)]

By proceeding in a way similar to Example 57, the dextrorotatory isomer of spiro[(5-methoxychroman)-3,2'-pyrrolidine] is obtained.

EXAMPLE 59: DEXTROROTATORY ISOMER OF SPIRO[(5-METHOXYCHROMAN)-3,2'-{N-[4'-(8'-AZASPIRO- [4',5']DECANE-7',9'-DION-8'-YL)-n-BUT-1'-YL]PYRROLIDINE}]

By proceeding as in Example 8 but starting with the levorotatory isomer of spiro[(5-methoxychroman)-3,2'-pyrrolidine], the dextrorotatory isomer of spiro- [(5-methoxychroman)-3,2'-{N-[4'-(8'- azaspiro[4',5']decane-7',9'-dion-8'-yl)-n-but-1'-yl ]pyrrolidine}] is obtained.

Melting point of the oxalate=72° C.
Pouvoir rotatoire [α]_D^{20}= +15° (19,6 mg dans 3 cm³ de chloroforme)

EXAMPLE 60: LEVOROTATORY ISOMER OF SPIRO[(5-METHOXYCHROMAN)-3,2'-{N-[4'-(8'-AZASPIRO-[4',5']DECANE-7',9'-DION-8'-YL)-n-BUT-1'-YL]PYRROLIDINE}]

By proceeding as in Example 8 but starting with the dextrorotatory isomer of spiro[(5-methoxychroman)-3,2'-pyrrolidine], the levorotatory isomer of spiro- [(5-methoxychroman)-3,2'-{N-[4'-(8'-azaspiro[4',5']-decane-7',9'-dion-8'-yl)-n-but-1'-yl]pyrrolidine}] is obtained.

Melting point of the oxalate=72° C.
Pouvoir rotatoire [α]_D^{20}= −16° (21,2 mg dans 3 cm³ de chloroforme)

EXAMPLE 61: SPIRO[(5-METHOXYCHROMAN)-3,2'-PIPERIDINE]

Stage I: Ethyl 3-(5-Methoxy-3-Nitrochroman-3-yl)-Butyrate

Add 0.02 cm³ of benzyltrimethylammonium methylate and then 0.585 g (3 mmol) of ethyl 4-bromobutyrate to a solution of 0.21 g (1 mmol) of 3-nitro-5-methoxychroman in 6 cm³ of N,N-dimethylformamide.

Heat to 60° C. for 15 hours, then dry at reduced pressure and purify the crude product obtained by chromatography on a silica column (eluent: methylene chloride).

0.145 g (45%) of ethyl 3-(5-methoxy-3-nitro-chroman-3-yl)butyrate are thus obtained in the form of colorless oil.

Infrared (film): 1725 cm$^{-1}$ v C=O
$^1$H NMR 300 MHz (CDCl$_3$) δ: ppm

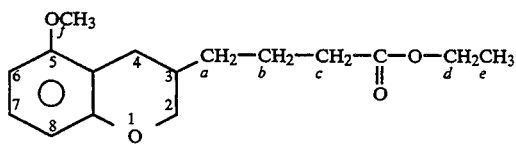

0.94, triplet J=7.2 Hz, 3H$_e$ 1.30 to 1.39, multiplet, 2H, H$_b$ 2.10 to 2.56, multiplet, 4H, H$_a$ and H$_c$ 2.89 and 3.60, 2 doublets J=17.5 Hz, 2H, H$_4$ 3.84, singlet, 3H, H$_f$ 4.09 and 4.57, 2 doublets, J=11.6 Hz, 2H, H$_2$ 4.12, quadruplet, J=7.2 Hz, 2H, H$_d$ 6.47 and 6.50, 2 doublets, J=8.3 Hz, 2H, H aromatic 7.11, triplet, J=8.3 Hz, 1H, H aromatic Stage II:
Spiro[(5-Methoxychroman)-3,2'-(Piperidin-6'-One)]

Dissolve 0.325 g (1 mmol) of ethyl 3-(5-methoxy-3-nitrochroman-3-yl)butyrate in 20 cm$^3$ of ethanol.

Add 40 mg of Raney nickel and heat to reflux under hydrogen atmosphere overnight.

After cooling, filter the reaction mixture on celite, then after drying the filtrate, purify the crude product obtained by chromatography on a silica column (eluent: 5 methanol/95 methylene chloride).

0.235 g (95%) of spiro[(5-methoxychroman)-3,2'-(piperidin-6'-one)] are thus obtained in the form of a colorless oil.

Infrared (film): 3245 cm$^{-1}$ v NH 1675 cm$^{-1}$ v C=O
$^1$H NMR 300 MHz (CDCl$_3$) δ: ppm

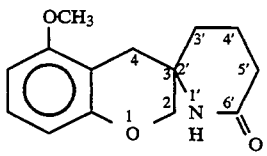

1.48 to 1.63, multiplet, 2H, H$_4'$ 1.90 to 2.10, multiplet, 2H, H$_3'$ 2.39 to 2.51, multiplet, 2H, H$_5'$ 2.75 to 2.87, 2 doublets, 2H, H$_4$ 3.83, singlet, 3H, H$_a$ 3.88 and 3.93, 2 doublets J=11.2 Hz, 2H, H$_2$ 5.80, unresolved bands, 1H, NH 6.46 and 6.52, 2 doublets, J=8.3 Hz, 2H, H aromatic 7.10, triplet, J=8.3 Hz, 1H, H aromatic Stage III: Spiro[(5-Methoxychroman)-3,2'-Piperidine]

Dissolve 0.25 g (1 mmol) of spiro[(5-methoxy-chroman)-3,2'-(piperidin-6'-one)] in 15 cm$^3$ of THF, then add the boranedimethyl sulfide complex and heat to reflux for 4 hours 30 min.

Dry the reaction mixture, take up the residue very slowly in 5 cm$^3$ of methanol and then add 2.5 cm$^3$ of 2M hydrochloric acid and heat to reflux for 90 minutes.

After cooling, remove the methanol, neutralize with a 2M aqueous sodium hydroxide solution, extract with methylene chloride.

The crude product obtained by drying is purified by chromatography on a silica column (eluent: 100% ethyl acetate).

0.160 g (70%) of spiro[(5-methoxychroman)-3,2'-piperidine] are thus obtained.

Infrared (film): 3300 cm$^{-1}$ v NH 1580 cm$^{-1}$ v C=C aromatic
$^1$H NMR 300 MHz (CDCl$_3$) δ: ppm

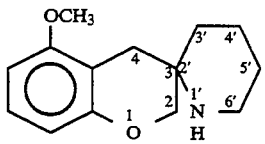

1.31 to 1.40, multiplet, 2H, H$_4'$ 1.56 to 1.97, multiplet, 4H, H$_5'$ and H$_3'$ 2.19, singlet, 1H, NH 2.68, singlet, 2H, H$_4$ 2.95 to 3.18, multiplet, 2H, H$_6'$ 3,81, singlet, 3H, H$_a$ 3,83, singlet, 2H, H2 6.44 and 6.53, 2 doublets, J=8.3 Hz, 2H, H aromatic 7.07, triplet, J=8.3 Hz, 1H, H aromatic EXAMPLE 62 to 69

By proceeding as in Examples 5, 8, 13, 17, 19, 20, 22, 24 and 27, but replacing spiro[(5-methoxychroman)-3,2'-pyrrolidine] with spiro[(5-methoxychroman)- 3,2'-piperidine] the following are obtained:

spiro[(5-methoxychroman)-3,2'-(N-propylpiperidine)]

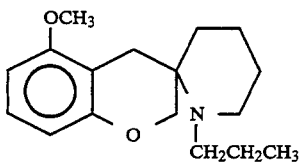

spiro[(5-methoxychroman)-3,2'-{N-[4'-(8'-azaspiro-[4',5']decane-7',9'-dion-8'-yl)-n-but-1'-yl ]piperidine}]

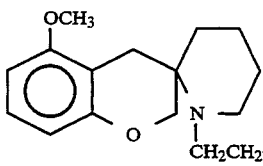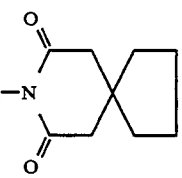

Infrared (film): 1655 and 1720 cm$^{-1}$ v C=O
spiro[(5-methoxychroman)-3,2'-[N-(4'-phthalimido-n- but-1'-yl)piperidine]]

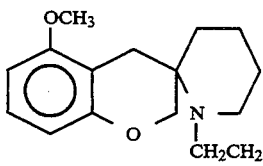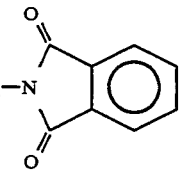

Infrared (film): 1705 cm$^{-1}$ v C=O
spiro[(5-methoxychroman)-3,2'-{N-[2'-(8'-azaspiro-[4',5']decane-7',9'-dion-8'-yl)ethyl ]piperidine}]

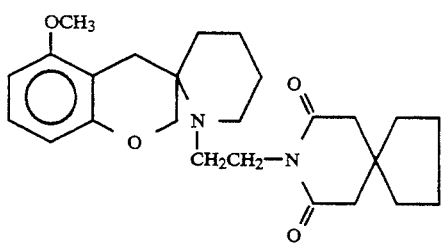

spiro[(5-methoxychroman)-3,2'-{N-[4'-(oxazolo[4',5'-b]pyridin-2' (3H)-on-3'-yl)-n-but-1'-yl ]piperidine}]

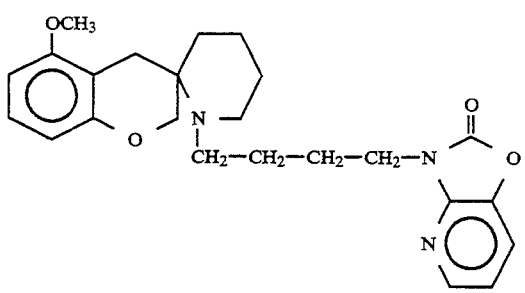

spiro[(5-methoxychroman)-3,2'-{N-[4'-(4',4'-dimethylpiperidine-2',6'-dion-1'-yl)-n-but-1'-yl]piperidine}]

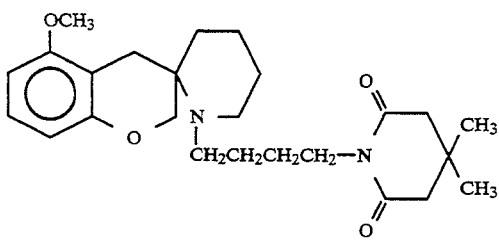

spiro[(5-methoxychroman)-3,2'-{N-[4'-(1',1'-dioxo-1',2'-benzisothiazol-3'(2H)-on-2'-yl)-n-but-1'-yl]piperidine}]

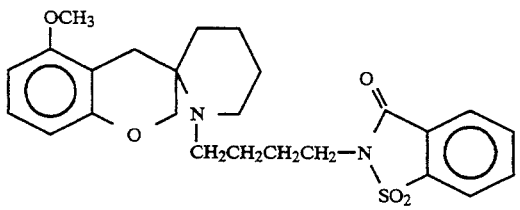

spiro[(5-methoxychroman)-3,2'-[N-benzylpiperidine)]

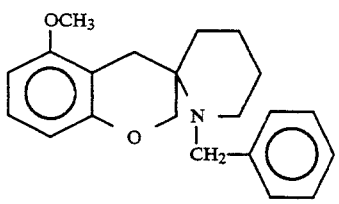

PHARMACOLOGICAL STUDY OF THE COMPOUNDS OF THE INVENTION

EXAMPLE 70: IN VITRO DETERMINATION OF THE AFFINITY OF THE COMPOUNDS OF THE INVENTION FOR SEROTONINERGIC, DOPAMINERGIC AND ALPHA ADRENERGIC RECEPTORS

The determinations of affinity for serotoninergic, dopaminergic and alpha adrenergic receptors were performed according to conventional techniques by displacement of a reference radio ligand.

| RECEPTOR | RADIOLIGAND | TISSUE USED |
|---|---|---|
| 5-HT$_1$A | 8-OH-DPAT | Hippocampus |
| 5-HT$_1$B | 5-OH-Tryptamine | Cortex + striatum + Globus Pallidus |
| 5-HT$_1$C | N-Methyl-Mesulergine | Cortex, hippocampus |
| 5-HT$_1$D | 5-OH-Tryptamine | Cortex + striatum + Globus Pallidus |
| 5-HT$_2$ | Kétansérin | Cortex |
| 5-HT$_3$ | BRL 43694 | Area postrema |

The results of these studies of binding show that the compounds of the invention have a high affinity associated with a strong selectivity for the 5-HT$_1$A receptors when compared with other serotoninergic receptors.

This selectivity for 5-HT$_1$A receptors is also very great (at least a factor of 1000) in relation to the D$_1$, D$_2$ dopaminergic and $\alpha_1$, $\alpha_2$ adrenergic receptors.

For example, spiro[(5-methoxychroman)-3,2'-{N-[4,-(8'-azaspiro[4',5']decane-7',9'-dion-8'-yl)-n-but-1'-yl]pyrrolidine}] has a nanomolar affinity for 5HT$_1$A receptors, whereas its affinity for the other serotoninergic receptors (5-HT$_1$B, 5-HT$_1$C, 5-HT$_1$D, 5-HT$_2$, 5HT$_3$) is between $4 \times 10^{-6}$M and $2 \times 10^{-5}$M and while its affinity for the other D$_1$, D$_2$, $\alpha_1$ and $\alpha_2$ receptors is less good than $10^{-6}$M.

EXAMPLE 71: ACUTE TOXICITY STUDY

The acute toxicity was determined after oral administration of increasing doses (0.1, 0.25, 0.50, 0.75 and 1 g/Kg$^{-1}$) of the products of the invention to batches of five mice (20±2 grams).

The animals were observed at regular intervals during the first day and daily for two weeks following the treatment. It is apparent that the compounds of the invention are completely nontoxic. No death is observed after the administration of a dose of 1 g.Kg$^{-1}$. No disorder is observed after the administration of this dose.

EXAMPLE 72: STUDY OF THE ANTIDEPRESSANT ACTIVITY EFFECT ON ESCAPE FAILURES

The study of the products is carried out on the model of "learned helplessness", which consists in inducing in the animal, by a series of uncontrollable aversive events, a defect during the subsequent avoidance tasks (Martin et al., 1986, Pharmacol. Biochem. Behav., 24, 177–181).

We use male Wistar A.F. rats obtained from CERJ homogeneous breedings, weighing between 180 and 200 grams. The animals are kept in the animal house for one week before the test, in plastic boxes, in groups of 10, at an ambient temperature of 21° C.±1° C., with free access to water and feed.

The animals are isolated in small boxes and subjected to 60 unavoidable electric shocks (0.8 mA every minute±15 seconds). A group of control rats does not receive electric shocks. The capacity of the animals to carry out an avoidance learning (shuttle-box) is assessed 48 hours later and during 3 consecutive days. During the learning sections, the animals undergo 2 tests per minute for 15 minutes. The number of escape failures is noted for each rat. The animals are treated (i.p.; 0.5 ml/100 g) 6 hours after the unavoidable shocks and for 4 days thereafter, in the morning 30 minutes before the shuttle-box session and the evening between 6 p.m. and 7 p.m.

The test products are dissolved in distilled water.

The test products are administered at doses of 0.25 mg. kg/day.

The test demonstrates the products of the invention significantly decrease the number of escape failures, thereby reflecting an activity of the antidepressant type.

EXAMPLE 73: PHARMACEUTICAL COMPOSITIONS

Tablets containing 2.5-mg doses of spiro[(5-methoxychroman)-3,2'-(N-[4'-(8'-azaspiro[4',5']decane-7',9'-dion-8-yl)-n-but-1'-yl ]pyrrolidine}]

Formula for 1000 tablets:

| | |
|---|---|
| Spiro [(5-methoxychroman)-3,2'-{N-[4'-(8'-azaspiro[4',5']decane-7',9'-dion-8'-yl)-n-but-1'-yl]pyrrolidine}] | 2.5 g |
| Wheat starch | 15 g |
| Corn starch | 15 g |
| Lactose | 65 g |
| Magnesium stearate | 2 g |
| Silica | 1 g |
| Hydroxypropyl cellulose | 2 g |

We claim:

1. A spirochroman compound selected from those of formula (I):

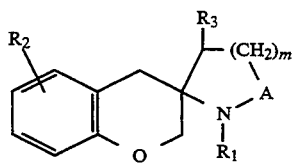

in which:
  m is 1 or 2,
  A denotes methylene ($CH_2$),
  $R_1$ denotes:
    linear or branched alkyl having 1 to 6 carbon atoms, inclusive, optionally substituted by: any one of the following groups:

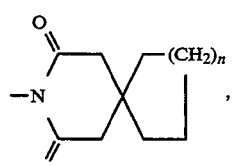

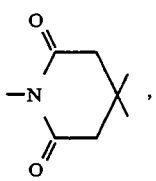

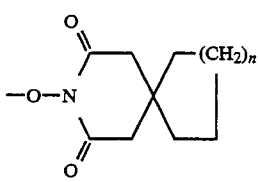

in which:
  n is 1 or 2,
  $R_2$ denotes:
    hydrogen,
    acetyl or a lower-alkoxy (1–6 C atoms) or hydroxyl,
  $R_3$ denotes hydrogen or linear or branched alkyl having 1 to 4 carbon atoms, inclusive,
  and pharmaceutically-acceptable inorganic or organic acid addition salts thereof.

2. A compound as claimed in claim 1, selected from those in which m is equal to 1, which corresponds to substituted spiro[chroman-3,2'-pyrrolidines] of following formula:

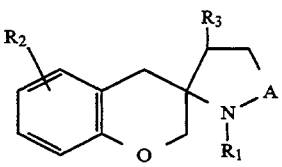

in which $R_1$, $R_2$, $R_3$ and A have the same meaning as in claim 1,
  and pharmaceutically-acceptable inorganic or organic acid addition salts thereof.

3. A compound as claimed in claim 1, selected from those in which m is equal to 2, which corresponds to substituted spiro[chroman-3,2'-piperidines] of following formula:

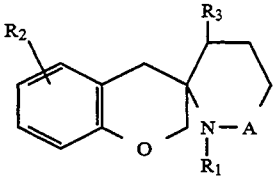

in which $R_1$, $R_2$, $R_3$ and A have the same meaning as in claim 1,
  and pharmaceutically-acceptable inorganic or organic acid addition salts thereof.

4. A compound as claimed in claim 1, which is selected from spiro[(5'methoxychroman)-3,2'-{N-[4'-(8'-azaspiro[4',5']decane-7',9'-dion-8'-yl)-n-but-1'-yl]pyrrolidine}] whose formula is shown below, and a salt of addition thereof to a pharmaceutically-acceptable inorganic or organic acid.

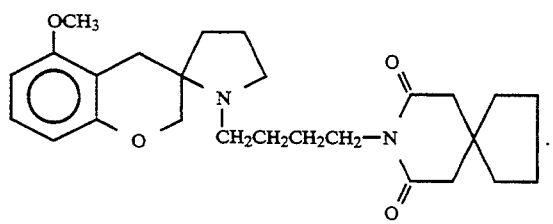

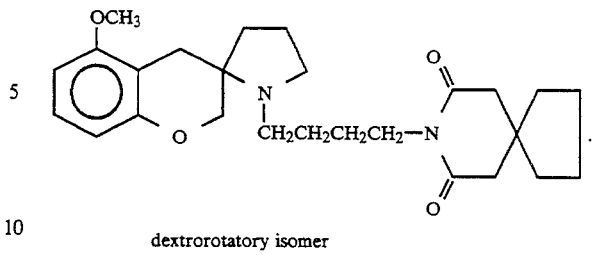

dextrorotatory isomer

5. A compound as claimed in claim 1, which is selected from the dextrorotatory isomer of spiro[(5-methoxychroman)-3,2'-{N-[4'-(8'-azaspiro[4',5']decane-7',9'-dion-8'-yl)-n-but- 1'-yl]pyrrolidine}] whose formula is shown below, and a salt of addition thereof to a pharmaceutically-acceptable inorganic or organic acid.

6. A pharmaceutical composition containing as active principle an effective antidepressive or anxiolytic amount of a compound as claimed in claim 1, in combination with one or more pharmaceutically-acceptable excipients or vehicles.

7. A method of treating a mammal afflicted with a disease selected from depression and anxiety comprising the step of administering to the said mammal an amount of a compound of claim 1 which is effective for alleviation of the said condition.

* * * * *

UNITED STATES PATENT AND TRADEMARK OFFICE
CERTIFICATE OF CORRECTION

PATENT NO. : 5,376,661
DATED : December 27, 1994
INVENTOR(S) : Gèrald Guillaumet, Tchao Podona, Gèrard Adam, Bèatrice Guardiola Pierre Renard It is certified that error appears in the above-indentified patent and that said Letters Patent is hereby corrected as shown below:

Column 4, line 10; insert the word "in" at the beginning of the line.

Column 12, line 31; "Infrared (film): 1720 cm$^{-1}$v C=O" and "1300 and 1170 cm$^{-1}$ v SO$_2$" should be two separate lines.
Column 13, line 38; insert a ")" before the hyphen at the end of the line.
Column 13, line 39; delete the ")" at the beginning of the line.
Column 14, line 67; "Infrared (KBr): 3250 cm$^{-1}$v NH" and "1670 cm$^{-1}$v C=O" should be two separate lines.
Column 15, line 8; "H$_3$40" should read -- H$_3{}'$ --
Column 15, line 21; "Infrared (KBr): 3225 cm$^{-1}$v NH" and "1675 cm$^{-1}$v C=O" should be two separate lines.
Column 16, line 66; "Infrared (film): 2960 to 2800 cm$^{-1}$v CH" and "1585 cm$^{-1}$v C=C aromatic" should be two separate lines.
Column 17, line 27; "Infrared (film): 2800 to 2980 cm$^{-1}$v CH" and "1575 cm$^{-1}$v C=C aromatic" should be two separate lines.
Column 18, line 40; "$^{31\ 1}$" should read -- $^{1}$ --
Column 18, line 56; insert an "H" between "2H," and "aromatic"
Column 20, line 3; insert a hyphen "-" between "1"and "yl]"

UNITED STATES PATENT AND TRADEMARK OFFICE
CERTIFICATE OF CORRECTION

PATENT NO. : 5,376,661
DATED : December 27, 1994
INVENTOR(S) : Gèrald Guillaumet, Tchao Podona, Gèrard Adam, Bèatrice Guardiola, Pierre Renard It is certified that error appears in the above-indentified patent and that said Letters Patent is hereby corrected as shown below:

Column 25, line 40 (in the formula) ; "CN" should read -- $NH_2$ --

Column 26, line 1; delete the space between "[N-" and "(2'-"
Column 26, line 14; insert ":" after "Example 36"
Column 26, line 15; delete the ":" at the beginning of the line.
Column 27, line 30 (the formula) ; there should be a "b" under the "$CH_3$" at the bottom of the formula.
Column 29, line 38; insert ":" between "56" and "SPIRO"
Column 29, line 56; "Infrared (film):2970 to 2810 $cm^{-1}v$ CH" and "1580 $cm^{-1}v$ C=C aromatic." should be two separate lines.
Column 31, line 16;"$3H_e$" should read -- 3H, $H_e$ --
Column 31, line 37; "Infrared (film): 3245 $cm^{-1}v$ NH" and "1675 $cm^{-1}v$ C=O" should be two separate lines.
Column 32, line 3; "Infrared (film): 3300 $cm^{-1}v$ NH" and "1580 $cm^{-1}v$ C=C aromatic" should be two separate lines.
Column 34, line 37; "$5HT_3$)" should read -- 5-$HT_3$) --
Column 36, line 64; "[(5'methoxychroman) should read -- [(5-methoxychroman) --

Signed and Sealed this

Ninth Day of May, 1995

BRUCE LEHMAN

*Attest:*

*Attesting Officer*   Commissioner of Patents and Trademarks

UNITED STATES PATENT AND TRADEMARK OFFICE
CERTIFICATE OF CORRECTION

PATENT NO. : 5,376,661

DATED : December 27, 1994

INVENTOR(S) : Gèrald Guillaumet, Tchao Podona, Gèrard Adam, Bèatrice Guardiola, Pierre Renard It is certified that error appears in the above-indentified patent and that said Letters Patent is hereby corrected as shown below:

Column 4, approximately line 53 (the formula); 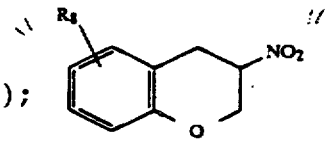

should read -- 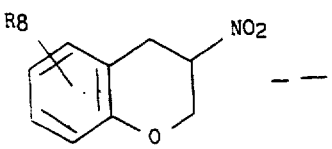 --

Signed and Sealed this

Sixth Day of June, 1995

Attest:

BRUCE LEHMAN

Attesting Officer

Commissioner of Patents and Trademarks